(12) United States Patent
Brunner et al.

(10) Patent No.: US 7,544,709 B2
(45) Date of Patent: Jun. 9, 2009

(54) DERIVATIVES OF ANDRIMIDE AND MOIRAMIDE B HAVING ANTIBACTERIAL PROPERTIES

(75) Inventors: Nina Brunner, Essen (DE); Christoph Freiberg, Wuppertal (DE); Thomas Lampe, Düsseldorf (DE); Ben Newton, Bucks (GB); Michael Otteneder, Arlesheim (AT); Josef Pernerstorfer, Hilden (DE); Jens Pohlmann, Wuppertal (DE); Guido Schiffer, Wuppertal (DE); Mitsuyuki Shimada, Nara (JP)

(73) Assignee: Bayer Healthcare AG, Leverkusen (DE)

( * ) Notice: Subject to any disclaimer, the term of this patent is extended or adjusted under 35 U.S.C. 154(b) by 701 days.

(21) Appl. No.: 10/496,058

(22) PCT Filed: Nov. 7, 2002

(86) PCT No.: PCT/EP02/12428

§ 371 (c)(1),
(2), (4) Date: Dec. 6, 2004

(87) PCT Pub. No.: WO03/043982

PCT Pub. Date: May 30, 2003

(65) Prior Publication Data

US 2005/0080129 A1    Apr. 14, 2005

(30) Foreign Application Priority Data

Nov. 20, 2001 (DE) ................................ 101 56 894

(51) Int. Cl.
*A61K 31/4015* (2006.01)
*C07D 207/40* (2006.01)

(52) U.S. Cl. .................................. 514/425; 548/546

(58) Field of Classification Search ................ 514/425; 548/546

See application file for complete search history.

(56) References Cited

U.S. PATENT DOCUMENTS 7,056,942 B2 *  6/2006  Hildesheim et al. ......... 514/411

FOREIGN PATENT DOCUMENTS

| EP | 0250115 A2 * | 6/1987 |
| EP | 0250115 | 12/1987 |
| JP | 1301657 | 12/1989 |

OTHER PUBLICATIONS

Patent Abstracts of Japan; vol. 014, No. 090 (C-0691), JP Application No. 63131043 (Publication No. 01301657).

McWhorter, et al., Stereocontrolled Synthesis of Andrimid and a Structural Requirement for the Activity, J. Chem. Society, Chem. Comm., 5: 299-301 (1989).

Needham, et al., Andrimid and Moiramides A-C, Metabolites Produced in Culture by a Marine Isolate of the Bacterium *Pseudomonas fluorescens*: Structure Elucidation and Biosynthesis, J. Org. Chem., 59(8): 2058-2063, 1994.

Ray, et al., Structures of Cyclic $C_4H_4$ Radical Cations, J. Am. Chem. Soc., 109: 4408-4411 (1987).

Singh, et al. Biological Activity and Mechanistic Studies of Andrimid, J. Antibiotics, 50 (3): 270-273 (1997).

Davies, et al. Asymmetric Syntheses of Moiramide B and Andrimid, J. Chem. Soc., Perkin Trans. 1, 2635-2643 (1998).

* cited by examiner

*Primary Examiner*—Rei-Tsang Shiao
*Assistant Examiner*—Joseph R Kosack
(74) *Attorney, Agent, or Firm*—Edwards Angell Palmer & Dodge LLP; Barry Kramer; Ralph A. Loren

(57) ABSTRACT

The invention relates to compounds of general formula (I), to a method for the production thereof, to pharmaceutical compositions containing them, and to their use in the treatment and/or prophlaxis of diseases in humans or animals, particularly bacterial infections diseases. The compounds are derivatives of the natural substances andrimide and moiramide B.

14 Claims, No Drawings

DERIVATIVES OF ANDRIMIDE AND MOIRAMIDE B HAVING ANTIBACTERIAL PROPERTIES

The present invention relates to compounds, to processes for preparing them, to pharmaceutical compositions comprising them, and to their use in the therapy and/or prophylaxis of illnesses in people or animals, especially diseases of bacterial infection.

The natural substances moiramide B ($R^a$=hydrogen, $R^b$=methyl) and andrimid ($R^a$=hydrogen, $R^b$=propenyl) have been described as having antibacterial activity, whereas moiramide C ($R^a$=hydroxyl, $R^b$=propenyl) is inactive. (A. Fredenhagen, S. Y. Tamura, P. T. M. Kenny, H. Komura, Y. Naya, K. Nakanishi, *J. Am. Chem. Soc.*, 1987, 109, 4409-4411; J. Needham, M. T. Kelly, M. Ishige, R. J. Andersen, *J. Org. Chem.*, 1994, 59, 2058-2063; M. P. Singh, M. J. Mroczenski-Wildey, D. A. Steinberg, R. J. Andersen, W. M. Maiese, M. Greenstein, *J. Antibiot.*, 1997, 50(3), 270-273). The isolation and antibacterial activity of andrimid is also described in EP-A-250 115. JP 01301657 describes the use of andrimid and certain amide-type derivatives as agrochemical antibiotics.

The synthesis of andrimid is described in A. V. Rama Rao, A. K. Singh, Ch. V. N. S. Varaprasad, *Tetrahedron Letters*, 1991, 32, 4393-4396, that of moiramide B and andrimid in S. G. Davies, D. J. Dixon, *J. Chem. Soc. Perkin Trans.* 1, 1998, 2635-2643.

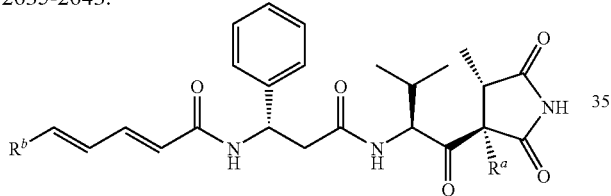

The properties of the natural substances, such as their activity, for example, do not meet the requirements imposed on antibacterial medicinal products. Although antibacterial products with different structures are on the market, a regular possibility is the development of resistance. New products for improved and effective therapy are therefore desirable.

It is an object of the present invention, therefore, to provide new and alternative compounds having equal or improved antibacterial action for treating bacterial diseases in people and animals.

Surprisingly it has been found that derivatives of this class of compound in which the beta-phenylalanine amide group is replaced by a urea group, a sulfonamide group or a carbamate group have antibacterial activity.

The present invention accordingly provides compounds of the general formula (I)

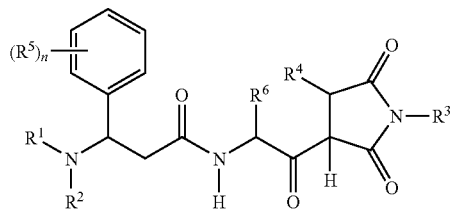

in which
$R^1$ is a group

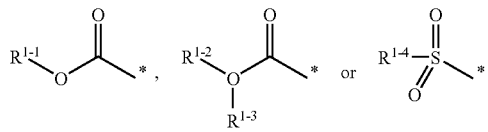

where
$R^{1-1}$ is alkyl, cycloalkyl or aryl, where
$R^{1-1}$ can optionally be substituted by from 1 to 3 substituents $R^{1-1-1}$, $R^{1-1-1}$ being selected independently at each occurrence from the group consisting of halogen, alkyl, aryl, alkoxy, phenoxy, amino, monoalkylamino, dialkylamino, aminocarbonyl, monoalkylaminocarbonyl, dialkylaminocarbonyl, carboxyl, alkoxycarbonyl, alkylcarbonyl, heteroaryl and heterocyclyl, $R^{1-2}$ and $R^{1-3}$ are identical or different and are hydrogen, alkyl, alkenyl, alkynyl, cycloalkyl, aryl, heteroaryl or heterocyclyl, where
$R^{1-2}$ can optionally be substituted by from 1 to 3 substituents $R^{1-2-1}$, $R^{1-2-1}$ being selected independently at each occurrence from the group consisting of halogen, trifluoromethyl, trifluoromethoxy, nitro, amino, alkyl, mono-alkylamino, dialkylamino, cycloalkyl, aryl, heteroaryl, heterocyclyl, hydroxyl, alkoxy, phenoxy, carboxyl, alkoxycarbonyl, alkylcarbonyl, aminocarbonyl, monoalkylaminocarbonyl, dialkylaminocarbonyl, aminosulfonyl, alkylamino-sulfonyl, dialkylaminosulfonyl, arylaminosulfonyl, heterocyclylamino-sulfonyl, heteroarylaminosulfonyl, aminocarbonylamino, hydroxycarbonylamino and alkoxycarbonylamino, it being possible for aryl and heteroaryl to be substituted by from 1 to 2 substituents selected independently of one another from the group consisting of halogen, hydroxyl, alkyl, alkoxy, trifluoromethyl, trifluoromethoxy, nitro, amino, cyano, monoalkylamino and dialkylamino, or
$R^{1-2}$ and $R^{1-3}$ together with the nitrogen atom to which they are attached form a heterocycle which can optionally be benzo-fused, $R^{1-4}$ is alkyl, alkenyl, alkynyl, cycloalkyl or aryl, where
$R^{1-4}$ can optionally be substituted by from 1 to 3 substituents $R^{1-4-1}$, $R^{1-4-1}$ being selected independently at each occurrence from the group consisting of halogen, alkyl, aryl, amino, monoalkylamino, dialkylamino, aminocarbonyl, monoalkylaminocarbonyl, dialkylaminocarbonyl, carboxyl, alkoxycarbonyl, alkylcarbonyl, heteroaryl and heterocyclyl, $R^2$ is hydrogen or methyl,
$R^3$ is hydrogen or $C_1$-$C_3$-alkyl,
$R^4$ is hydrogen or $C_1$-$C_3$-alkyl,
$R^5$ is selected from the group consisting of halogen, trifluoromethyl, trifluoromethoxy, nitro, amino, monoalkylamino, dialkylamino, hydroxyl, alkyl, alkoxy, carboxyl, alkoxycarbonyl, aminocarbonyl, monoalkylamino-carbonyl, dialkylaminocarbonyl, aryl and heteroaryl, or two substituents $R^5$ together with the carbon atoms to which they are attached form a cycloalkyl or heterocyclyl, it being possible for this cycloalkyl or heterocyclyl to be substituted by 0, 1 or 2 substituents $R^{5-1}$, the substituents $R^{5-1}$ being selected independently of one another from the group consisting of halogen, alkyl, nitro, amino, trifluoromethyl, hydroxyl and alkoxy, n is 0, 1, 2 or 3, where if n is 2 or 3 the radicals $R^5$ can be identical or different, $R^6$ is alkyl, cycloalkyl or heterocyclyl, it being possible for $R^6$ to be substituted by 0, 1 or 2 substituents $R^{6-1}$, the substituents $R^{6-1}$ being selected independently of one another from the group consisting of halogen, nitro, amino, trifluoromethyl, hydroxyl, alkyl and alkoxy, and also their pharmaceutically compatible salts, solvates and hydrates.

The compounds of the general formula (I) according to the invention may occur in various stereoisomeric forms, the relationship of which to one another is either that of image and mirror image (enantiomers) or is not that of image and mirror image (diastereomers). The invention relates both to the enantiomers and to the diastereomers, and also to their respective mixtures. The racemic forms, like the diastereoisomers, can be resolved into the stereoisomerically uniform constituents in a known manner.

It is additionally possible for certain compounds to exist in tautomeric forms. This is known to the skilled worker, and such compounds are likewise embraced by the extent of the invention.

The substances of the general formula (I) according to the invention can also be in the form of salts. In the context of the invention physiologically unobjectionable salts are preferred.

Pharmaceutically compatible salts can be salts of the compounds of the invention with organic or inorganic acids. Preference is given to salts with inorganic acids such as hydrochloric acid, hydrobromic acid, phosphoric acid or sulfuric acid, for example, or to salts with organic carboxylic or sulfonic acids such as acetic acid, propionic acid, maleic acid, fumaric acid, malic acid, citric acid, tartaric acid, lactic acid, benzoic acid, or methanesulfonic acid, ethanesulfonic acid, benzenesulfonic acid, toluenesulfonic acid or naphthalenedisulfonic acid.

Pharmaceutically compatible salts can also be salts of the compounds of the invention with bases, such as metal salts or ammonium salts, for example. Preferred examples are alkali metal salts (e.g., sodium or potassium salts), alkaline earth metal salts (e.g., magnesium or calcium salts), and ammonium salts derived from ammonia or organic amines, such as ethylamine, diethylamine or triethylamine, ethyldiisopropylamine, monoethanolamine, di- or triethanolamine, dicyclohexylamine, dimethylamino-ethanol, dibenzylamine, N-methylmorpholine, dihydroabietylamine, 1-ephenamine, methylpiperidine, arginine, lysine, ethylenediamine or 2-phenylethylamine.

The compounds of the present invention are distinguished by a broad spectrum of activity against Gram-positive and Gram-negative bacteria, which may also extend to multi-resistant microbes, particularly staphylococci, pneumococci and enterococci, including vancomycin-resistant strains.

Alkyl and also the alkyl moieties in alkoxy, mono- and dialkylamino and alkylsulfonyl stands for linear or branched alkyl and, unless otherwise specified, includes $C_1$-$C_6$-alkyl, especially methyl, ethyl, propyl, isopropyl, butyl and isobutyl.

Alkenyl embraces linear and branched $C_2$-$C_6$ and $C_2$-$C_4$-alkenyl, such as vinyl, allyl, prop-1-en-1-yl, isopropenyl, but-1-enyls, but-2-enyls, buta-1,2-dienyls, and buta-1,3-dienyls.

Alkynyl embraces linear and branched $C_2$-$C_6$ and $C_2$-$C_4$-alkynyl, such as ethynyl, n-prop-2-yn-1-yl, and n-but-2-yn-1-yl.

Cycloalkyl embraces monocyclic $C_3$-$C_8$-alkyl, such as cyclopropyl, cyclobutyl, cyclopentyl, cyclohexyl, cycloheptyl, and cyclooctyl.

Alkoxy in the context of the invention preferably stands for a straight-chain or branched alkoxy radical having in particular 1 to 6, 1 to 4 or 1 to 3 carbon atoms. Preference is given to a straight-chain or branched alkoxy radical having 1 to 3 carbon atoms. Preferred examples that may be mentioned include the following: methoxy, ethoxy, n-propoxy, isopropoxy, t-butoxy, n-pentoxy, and n-hexoxy.

Alkoxycarbonyl in the context of the invention stands preferably for a straight-chain or branched alkoxy radical having 1 to 6 or 1 to 4 carbon atoms which is linked via a carbonyl group. Preference is given to a straight-chain or branched alkoxycarbonyl radical having 1 to 4 carbon atoms. Preferred examples that may be mentioned include the following: methoxycarbonyl, ethoxycarbonyl, n-propoxycarbonyl, isopropoxy-carbonyl, and t-butoxycarbonyl.

Monoalkylamino in the context of the invention stands for an amino group having a straight-chain or branched alkyl substituent which has preferably 1 to 6, 1 to 4 or 1 to 2 carbon atoms. Preference is given to a straight-chain or branched monoalkylamino radical having 1 to 4 carbon atoms. Preferred examples that may be mentioned include the following: methylamino, ethylamino, n-propylamino, isopropylamino, t-butylamino, n-pentylamino, and n-hexylamino.

Dialkylamino in the context of the invention stands for an amino group having two identical or different straight-chain or branched alkyl substituents, which preferably each have 1 to 6, 1 to 4 or 1 to 2 carbon atoms. Preference is given to straight-chain or branched dialkylamino radicals having in each case 1 to 4 carbon atoms. Preferred examples that may be mentioned include the following: N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino, and N-n-hexyl-N-methylamino.

Mono- or dialkylaminocarbonyl in the context of the invention stands for an amino group which is linked via a carbonyl group and which has one straight-chain or branched or two identical or different straight-chain or branched alkyl substituent(s) having preferably in each case 1 to 4 or 1 to 2 carbon atoms. Preferred examples that may be mentioned include the following: methylaminocarbonyl, ethylaminocarbonyl, isopropylaminocarbonyl, t-butylaminocarbonyl, N,N-dimethylaminocarbonyl, N,N-diethylaminocarbonyl, N-ethyl-N-methylaminocarbonyl, and N-t-butyl-N-methylaminocarbonyl.

Alkylcarbonylamino (acylamino) in the context of the invention stands for an amino group having a straight-chain or branched alkanoyl substituent which contains preferably 1 to 6, 1 to 4 or 1 to 2 carbon atoms and is linked via the carbonyl group. Preference is given to a monoacylamino radical having 1 to 2 carbon atoms. Preferred examples that may be mentioned include the following: formamido, acetamido, propionamido, n-butyramido, and pivaloylamido.

Alkoxycarbonylamino in the context of the invention stands for an amino group having a straight-chain or branched alkoxycarbonyl substituent which preferably has 1 to 6 or 1 to 4 carbon atoms in the alkoxy radical and is linked via the carbonyl group. Preference is given to an alkoxycarbonylamino radical having 1 to 4 carbon atoms. Preferred examples that may be mentioned include the following: methoxycarbonylamino, ethoxycarbonylamino, n-propoxycarbonylamino, and t-butoxycarbonylamino.

Aminosulfonyl stands for an —S(O)$_2$NH$_2$ group. Accordingly alkylaminosulfonyl, dialkylaminosulfonyl, arylaminosulfonyl, heterocyclylaminosulfonyl, and heteroaryl-aminosulfonyl are substituted on the amino group with the corresponding radicals, i.e., alkyl, aryl, etc.

Aryl stands in general for an aromatic radical having 6 to 10 carbon atoms. Preferred aryl radicals are phenyl and naphthyl.

Heteroaryl (heteroaromatic) stands for a 5- to 10-membered aromatic heterocycle having up to 3 heteroatoms from the series S, O and/or N, for example, for pyridyl, pyrimidyl, thienyl, furyl, pyrrolyl, thiazolyl, N-triazolyl, oxazolyl or imidazolyl. Preference is given to pyridyl, furyl, thienyl, and thiazolyl.

Heterocyclyl (heterocycle) stands for a 3- to 8-membered saturated or unsaturated, nonaromatic heterocycle which is optionally attached via a nitrogen atom and may contain up to 3 heteroatoms from the series S, O and N. It may be formed from two substituent groups together with the nitrogen atom to which they are attached, and includes, for example, morpholinyl, piperidinyl, piperazinyl, methylpiperazinyl, thiomorpholinyl, or pyrrolidinyl, and also 3-, 7-, and 8-membered heterocycles, such as aziridines (e.g., 1-azacyclopropan-1-yl), azetidines (e.g., 1-azacyclobutan-1-yl), and azepines (e.g., 1-azepan-1-yl). The unsaturated representatives can contain 1 to 2 double bonds in the ring.

Halogen stands for fluorine, chlorine, bromine or iodine, fluorine and chlorine being preferred, unless indicated otherwise.

Benzo-fused in the context of the invention stands for a phenyl which is attached via two carbon atoms to a heterocycle or a cycloalkyl.

The general definitions of radicals listed above, or those definitions of radicals that are indicated in ranges of preference, apply both to the end products of the formula (I) and, correspondingly, to the starting materials and/or intermediates required in each case for the preparation.

The definitions of radicals indicated individually in the respective combinations or preferred combinations of radicals are arbitrarily also replaced by definitions of radicals of other combinations, irrespective of the particular radical combinations indicated.

In a further embodiment the invention relates to compounds of general formula (I)

in which
$R^{1-1}$ is alkyl, cycloalkyl or aryl, where
$R^{1-1}$ can be optionally substituted by from 1 to 3 substituents $R^{1-1-1}$, $R^{1-1-1}$ being selected independently at each occurrence from the group consisting of halogen, alkyl, aryl and alkoxy,
$R^{1-2}$ and $R^{1-3}$ are identical or different and are hydrogen, alkyl, alkenyl, cycloalkyl, aryl or heteroaryl,
it being possible for $R^{1-2}$ to be substituted by from 1 to 2 substituents $R^{1-2-1}$ $R^{1-2-1}$ being selected independently at each occurrence from the group consisting of halogen, trifluoromethyl, trifluoromethoxy, nitro, amino, alkyl, monoalkylamino, dialkylamino, cycloalkyl, aryl, heteroaryl, heterocyclyl, hydroxyl, alkoxy, phenoxy, alkylcarbonyl, aminocarbonyl, monoalkylamino-carbonyl, dialkylaminocarbonyl and aminosulfonyl, it being possible for aryl and heteroaryl to be substituted by from 1 to 2 substituents selected independently of one another from the group consisting of halogen, hydroxyl, alkoxy, trifluoromethyl, trifluoromethoxy, nitro and amino,
or $R^{1-2}$ and $R^{1-3}$ together with the nitrogen atom to which they are attached form a heterocycle which can optionally be benzo-fused,
$R^{1-4}$ is alkyl, alkenyl or aryl, where
$R^{1-4}$ can optionally be substituted by from 1 to 3 substituents $R^{1-4-1}$, $R^{1-4-1}$ being selected independently at each occurrence from the group consisting of halogen, alkyl and aryl,
$R^2$ is hydrogen,
$R^3$ is hydrogen or methyl,
$R^4$ is methyl,
$R^5$ is selected from the group consisting of fluorine, chlorine, trifluoromethyl, trifluoromethoxy, nitro, amino, monoalkylamino, dialkylamino, hydroxyl, alkyl, alkoxy, alkoxycarbonyl, aminocarbonyl, phenyl, and 5- to 6-membered heteroaryl, or two substituents $R^5$ together with the carbon atoms to which they are attached form a cycloalkyl or heterocyclyl,
n is 0, 1 or 2, where if n is 2 the radicals $R^5$ can be identical or different,
$R^6$ is alkyl or cycloalkyl,
where $R^6$ can be substituted by 0, 1 or 2 substituents $R^{6-1}$, the substituents $R^{6-1}$ being selected independently of one another from the group consisting of halogen, trifluoromethyl and alkoxy, and also their pharmaceutically compatible salts, solvates and hydrates.

In a further embodiment the invention relates to the compounds of the general formula (I), in which
$R^{1-1}$ is $C_1$-$C_4$-alkyl, cyclopentyl, cyclohexyl, phenyl or naphthyl, where
$R^{1-1}$ can optionally be substituted by from 1 to 2 substituents $R^{1-1-1}$, $R^{1-1-1}$ being selected independently at each occurrence from the group consisting of fluorine, chlorine, methyl, ethyl, phenyl, methoxy and ethoxy,
$R^{1-2}$ is alkyl, alkenyl, cycloalkyl, aryl or heteroaryl,
it being possible for $R^{1-2}$ to be optionally substituted by 1 substituent $R^{1-2-1}$, $R^{1-2-1}$ being selected from the group consisting of fluorine, chlorine, trifluoromethyl, amino, alkyl, monoalkylamino, dialkylamino, alkylcarbonyl, aryl, heteroaryl, hydroxyl, methoxy and phenoxy, it being possible for aryl and heteroaryl to be substituted by 1 substituent selected from the group consisting of halogen, methoxy, trifluoromethyl and amino,
$R^{1-3}$ is hydrogen or methyl,
or $R^{1-2}$ and $R^{1-3}$ together with the nitrogen atom to which they are attached form a heterocycle which can optionally be benzo-fused,
$R^{1-4}$ is alkyl, alkenyl or phenyl, where
$R^{1-4}$ can optionally be substituted by 1 substituent $R^{1-4-1}$, $R^{1-4-1}$ being selected from the group consisting of fluorine, chlorine and phenyl,
$R^2$ is hydrogen,
$R^3$ is hydrogen,
$R^4$ is methyl, $R^5$ is selected from the group consisting of fluorine, chlorine, trifluoromethyl, alkoxy, methoxycarbonyl, $C_1$-$C_4$-alkyl, phenyl and pyridyl, n is 0, 1 or 2, where if n is 2 the radicals $R^5$ can be identical or different, $R^6$ is isopropyl, isobutyl, isopentyl or cyclopentyl, and also their pharmaceutically acceptable salts, solvates and hydrates.

Preference is given in the context of the present invention to compounds of the general formula (I) which have the general formula (Ic):

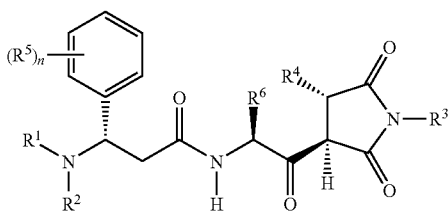

(Ic)

where $R^1$ to $R^6$ and n are as defined above.

Preference in the context of the present inventions is also given to compounds of the general formula (I) in which $R^{1-2}$ is alkyl, alkenyl, cycloalkyl or aryl, where $R^{1-2}$ can optionally be substituted by from 1 to 2, in particular one, substituent(s) $R^{1-2-1}$, $R^{1-2-1}$ being selected from the group consisting of halogen, nitro, amino, alkyl, aryl, heteroaryl, hydroxyl, alkoxy, carboxyl, alkylcarbonyl, alkoxycarbonyl and aminocarbonyl, in particular selected from the group consisting of alkyl, aryl, heteroaryl and alkoxy.

In a further embodiment the invention relates to compounds of the general formula (Ia),

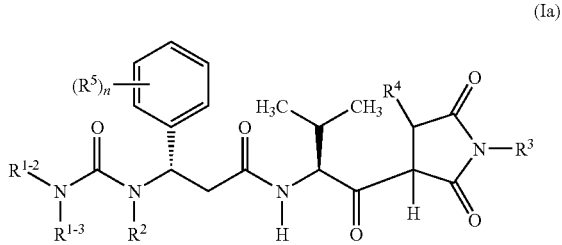

(Ia)

in which $R^{1-2}$ and $R^{1-3}$ are identical or different and are hydrogen, alkyl, alkenyl, alkynyl, cycloalkyl, aryl, heteroaryl or heterocyclyl, it being possible for $R^{1-2}$ to be optionally substituted by from 1 to 3 substituents $R^{1-2-1}$, $R^{1-2-1}$ being selected independently at each occurrence from the group consisting of halogen, trifluoromethyl, trifluoromethoxy, nitro, amino, monoalkylamino, dialkylamino, cycloalkyl, aryl, heteroaryl, heterocyclyl, hydroxyl, alkoxy, carboxyl, alkoxycarbonyl, aminocarbonyl, monoalkylaminocarbonyl, dialkylaminocarbonyl, aminosulfonyl, alkylamino-sulfonyl, dialkylaminosulfonyl, arylaminosulfonyl, heterocyclylamino-sulfonyl, heteroarylaminosulfonyl, aminocarbonylamino, hydroxycarbonyl-amino and alkoxycarbonylamino, it being possible for aryl and heteroaryl to be substituted by from 1 to 2 substituents selected independently of one another from the group consisting of halogen, hydroxyl, alkoxy, trifluoromethyl, trifluoromethoxy, nitro, amino, cyano, monoalkylamino and dialkylamino, or $R^{1-2}$ and $R^{1-3}$ together with the nitrogen atom to which they are attached form a heterocycle, $R^2$ is hydrogen or methyl, $R^3$ is hydrogen or $C_1$-$C_3$-alkyl, $R^4$ is hydrogen or $C_1$-$C_3$-alkyl, $R^5$ is selected from the group consisting of halogen, trifluoromethyl, trifluoromethoxy, nitro, amino, monoalkylamino, dialkylamino, hydroxyl, alkoxy, carboxyl, alkoxycarbonyl, aminocarbonyl, monoalkylaminocarbonyl and dialkylaminocarbonyl, n is 0, 1, 2 or 3, where if n is 2 or 3 the radicals $R^5$ can be identical or different, and also their pharmaceutically acceptable salts, solvates and hydrates.

In a further embodiment the invention relates to compounds of the general formula (Ia)

in which $R^{1-2}$ and $R^{1-3}$ are identical or different and are hydrogen, alkyl, alkenyl, aryl or heteroaryl, it being possible for $R^{1-2}$ to be optionally substituted by from 1 to 2 substituents $R^{1-2-1}$, $R^{1-2-1}$ being selected independently at each occurrence from the group consisting of halogen, trifluoromethyl, trifluoromethoxy, nitro, amino, monoalkylamino, dialkylamino, cycloalkyl, aryl, heteroaryl, heterocyclyl, hydroxyl, alkoxy, aminocarbonyl, monoalkylaminocarbonyl, dialkylaminocarbonyl and aminosulfonyl, it being possible for aryl and heteroaryl to be substituted by from 1 to 2 substituents selected independently of one another from the group consisting of halogen, hydroxyl, alkoxy, trifluoromethyl, trifluoromethoxy, nitro and amino, or $R^{1-2}$ and $R^{1-3}$ together with the nitrogen atom to which they are attached form a heterocycle, $R^2$ is hydrogen, $R^3$ is hydrogen or methyl, $R^4$ is $C_1$-$C_3$-alkyl, $R^5$ is selected from the group consisting of fluorine, chlorine, trifluoromethyl, trifluoromethoxy, nitro, amino, monoalkylamino, dialkylamino, hydroxyl, alkoxy and aminocarbonyl, n is 0, 1 or 2, where if n is 2 the radicals $R^5$ can be identical or different, and also their pharmaceutically acceptable salts, solvates and hydrates.

In a further embodiment the invention relates to compounds of the general formula (Ia)

in which $R^{1-2}$ is alkyl, alkenyl, aryl or heteroaryl, it being possible for $R^{1-2}$ to be optionally substituted by 1 substituent $R^{1-2-1}$, $R^{1-2-1}$ being selected from the group consisting of fluorine, chlorine, trifluoromethyl, amino, monoalkylamino, dialkylamino, aryl, heteroaryl, hydroxyl and methoxy, it being possible for aryl and heteroaryl to be substituted by 1 substituent selected from the group consisting of halogen, hydroxyl, alkoxy, trifluoromethyl and amino, $R^{1-3}$ is hydrogen or methyl, or $R^{1-2}$ and $R^{1-3}$ together with the nitrogen atom to which they are attached form a heterocycle, $R^2$ is hydrogen, $R^3$ is hydrogen, $R^4$ is methyl, $R^5$ is selected from the group consisting of fluorine, chlorine, trifluoromethyl, amino, monoalkylamino, dialkylamino, hydroxyl and alkoxy, n is 0, 1 or 2, where if n is 2 the radicals $R^5$ can be identical or different, and also their pharmaceutically acceptable salts, solvates and hydrates.

Preference is given in the context of the present invention to compounds of the general formula (I) which have the general formula (Ib):

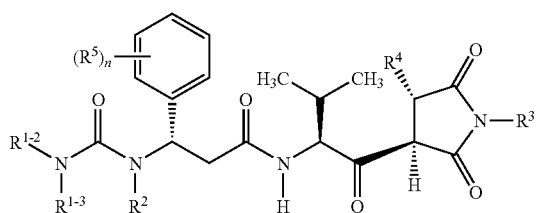

(Ib)

in which $R^{1-2}$ to $R^5$ and n are as defined above.

Preference in the context of the present inventions is also given to compounds of the general formula (I) in which $R^1$ is a group

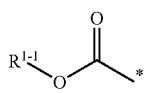

where $R^{1-1}$ is $C_1$-$C_4$-alkyl.

Preference in the context of the present inventions is also given to compounds of the general formula (I) in which $R^1$ is a group

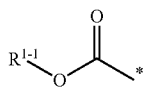

where $R^{1-1}$ is phenyl or naphthyl, it being possible for $R^{1-1}$ to be substituted optionally by from 1 to 2 substituents $R^{1-1-1}$, $R^{1-1-1}$ being selected independently at each occurrence from the group consisting of fluorine, chlorine, methyl, ethyl, phenyl, methoxy and ethoxy.

Preference in the context of the present inventions is also given to compounds of the general formula (I), (Ia), (Ib) or (Ic) in which $R^1$ is a group

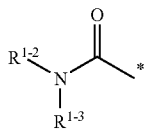

where $R^{1-2}$ is alkyl, alkenyl or aryl, it being possible for $R^{1-2}$ to be optionally substituted by from 1 to 2, in particular one, substituent(s) $R^{1-2-1}$, $R^{1-2-1}$ being selected from the group consisting of halogen, nitro, amino, aryl, heteroaryl, hydroxyl, alkoxy, carboxyl, alkoxycarbonyl and amino-carbonyl, in particular selected from the group consisting of aryl, heteroaryl and alkoxy.

Preference in the context of the present inventions is also given to compounds of the general formula (I), (Ia), (Ib) or (Ic)

in which $R^1$ is a group

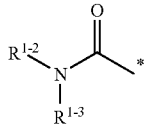

where $R^{1-3}$ is hydrogen or methyl.

Preference in the context of the present inventions is also given to compounds of the general formula (I) in which $R^1$ is a group

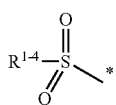

where $R^{1-4}$ is alkyl.

Preference in the context of the present inventions is also given to compounds of the general formula (I) in which $R^1$ is a group

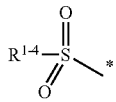

where $R^{1-4}$ is alkenyl or phenyl, it being possible for $R^{1-4}$ to be optionally substituted by 1 substituent $R^{1-4-1}$, $R^{1-4-1}$ being selected from the group consisting of fluorine, chlorine and phenyl.

Preference in the context of the present inventions is also given to compounds of the general formula (I), (Ia), (Ib) or (Ic) in which $R^2$ is hydrogen.

Preference in the context of the present inventions is also given to compounds of the general formula (I), (Ia), (Ib) or (Ic) in which $R^3$ is hydrogen.

Preference in the context of the present inventions is also given to compounds of the general formula (I), (Ia), (Ib) or (Ic) in which $R^4$ is methyl.

Preference in the context of the present inventions is also given to compounds of the general formula (I), (Ia), (Ib) or (Ic) in which $R^5$ is hydrogen.

Preference in the context of the present inventions is also given to compounds of the general formula (I) or (Ic) in which $R^6$ is alkyl or cycloalkyl.

Preference in the context of the present inventions is also given to compounds of the general formula (I) or (Ic) in which R is isopropyl.

Preference in the context of the present inventions is also given to the following compounds:
(S)-3-(3-benzylureido)-N-{(S)-2-methyl-1-[1-((3R,4S)-4-methyl-2,5-dioxopyrrolidin-3-yl)methanoyl]propyl}-3-phenylpropionamide,
(S)-3-[3-(4-methoxyphenyl)ureido]-N-{(S)-2-methyl-1-[1-((3R,4S)-4-methyl-2,5-dioxopyrrolidin-3-yl)methanoyl]propyl}-3-phenylpropionamide,
(S)-N-{(S)-2-methyl-1-[1-((3R,4S)-4-methyl-2,5-dioxopyrrolidin-3-yl)methanoyl]propyl}-3-(3-methyl-3-phenylureido)-3-phenylpropionamide,
N-((1S)-2-methyl-1-{[(3R,4S)-4-methyl-2,5-dioxo-3-pyrrolidinyl]carbonyl}propyl)-3-{[(1-naphthylamino)carbonyl]amino}-3-phenylpropionamide,
3-[({[4-chloro-3-(trifluoromethyl)phenyl]amino}carbonyl)amino]-N-((1S)-2-methyl-1-{[(3R,4S)-4-methyl-2,5-dioxo-3-pyrrolidinyl]carbonyl}propyl)-3-phenyl-propionamide,
tert-butyl (1S)-3-({1-cyclopentyl-2-[(3R,4S)-4-methyl-2,5-dioxo-3-pyrrolidinyl]-2-oxoethyl}amino)-3-oxo-1-phenylpropylcarbamate,
(R,2S)-N-(3-{[(1,1'-biphenyl-4-yloxy)carbonyl]amino}-3-phenylpropanoyl)-(3R,4S)-3-[(R)-N-(3-{[(1,1'-biphenyl-4-yloxy)carbonyl]amino}-3-phenylpropanoyl)-L-valyl]-4-methyl-2,5-dioxo-2-pyrrolidinyl-{(3S,4R)-4-[(R)-N-(3-{[(1,1'-biphenyl-4-yloxy)-carbonyl]amino}-3-phenylpropanoyl)-L-valyl]-3-methyl-2,5-dioxo-3-pyrrolidinyl}-L-valine {2-[(S)-2-methyl-1-((3R,4S)-4-methyl-2,5-dioxo-pyrrolidin-3-carbonyl)-propylcarbamoyl]-1-phenyl-ethyl}carbamic acid biphenyl-4-yl ester.
(3S)-N-((1S)-2-Methyl-1-{[(3R,4S)-4-methyl-2,5-dioxo-3-pyrrolidinyl]carbonyl}-propyl)-3-phenyl-3-({[(E)-2-phenylethenyl]sulfonyl} amino)propionamide.

The present invention further relates to a process for preparing the compounds of the general formula (I), in which compounds of the general formula (II)

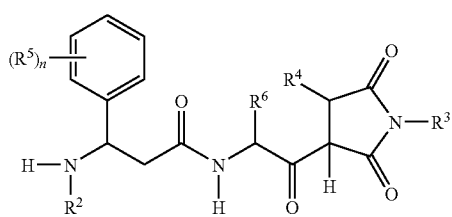

(II)

in which
$R^2$ to $R^6$ and n are as defined above, which may optionally be present in the form of their salts, for the case where
$R^1$ is a group

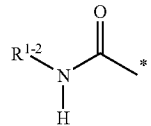

in which $R^{1-2}$ is as defined above,
[A] are reacted with compounds of the general formula (IIIa)

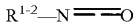  (IIIa)

in which
$R^{1-2}$ is as defined above,
or, for the case where
$R^1$ is a group

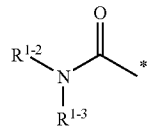

where
$R^{1-3}$ is not hydrogen, or $R^{1-2}$ and $R^{1-3}$ form a heterocycle,
[B] are reacted with compounds of the general formula (IIIb)

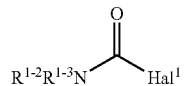  (IIIb)

in which
$R^{1-2}$ and $R^{1-3}$ are as defined above and $Hal^1$ stands for a halide or another leaving group,
or, for the case where
$R^1$ is a group

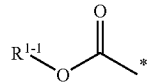

in which
$R^{1-1}$ is as defined above,
[C] are reacted with compounds of the general formula (IIIc)

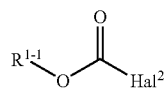  (IIIc)

in which
$R^{1-1}$ is as defined above and $Hal^2$ stands for a halide or another leaving group,
or, for the case where
$R^1$ is a group

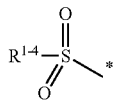

in which $R^{1-4}$ is as defined above,
[D] are reacted with compounds of the general formula (IIId)

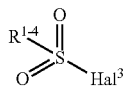

(IIId)

in which
$R^{1-4}$ is as defined above and $Hal^3$ stands for a halide or another leaving group.

The reaction according to processes [A] to [D] takes place generally in the presence of a solvent, where appropriate in the presence of a base.

Bases are, for example, alkali metal carbonates such as cesium carbonate, sodium or potassium carbonate, or potassium tert-butoxide, or tertiary amine bases such as triethylamine or diisopropylethylamine, or polymer-bound amine bases such as PS-DIEA, or other bases such as DBU, preference being given to triethylamine, diisopropylethylamine or PS-DIEA.

Suitable solvents here are inert organic solvents which do not change under the reaction conditions. They include halogenated hydrocarbons such as dichloro-methane, trichloromethane or dichloroethane, hydrocarbons such as benzene, xylene, toluene, hexane, cyclohexane or petroleum fractions, nitromethane, dimethyl-formamide or acetonitrile, or ethers such as diethyl ether, tetrahydrofuran or dioxane. It is also possible to use mixtures of the solvents. Particular preference is given to dichloromethane, dichloroethane, tetrahydrofuran or dimethylformamide.

The compounds of the general formula (II) are known from the literature or are new and can be prepared by adding acid, particularly hydrochloric acid or trifluoroacetic acid, to compounds of the general formula (Id)

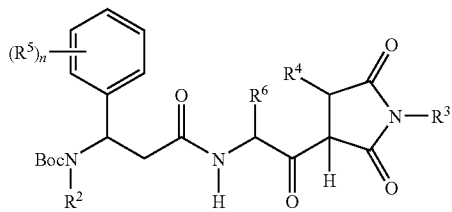

(Id)

in which
$R^2$ to $R^6$ and n are as defined above.

Suitable solvents here are inert organic solvents which do not change under the reaction conditions. They include halogenated hydrocarbons such as dichloromethane or trichloromethane, hydrocarbons such as benzene, xylene, toluene, hexane, cyclohexane, or petroleum fractions, nitromethane, dimethylformamide or acetonitrile, or ethers such as diethyl ether, tetrahydrofuran or dioxane. It is also possible to use mixtures of the solvents. Particular preference is given to the use of hydrochloric acid in dioxane or trifluoroacetic acid in dichloromethane.

The compounds of the general formula (Id) represent a specific embodiment of the compound of general formula (I).

The compounds of the general formula (Id) are known from the literature or are new and can be prepared by reacting compounds of the general formula (V)

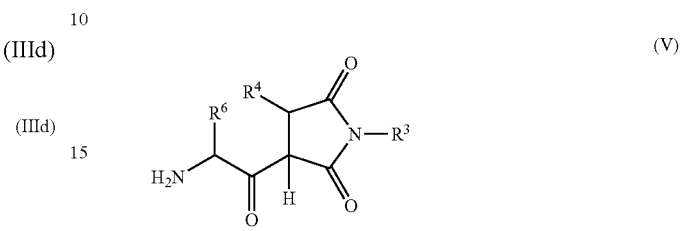

(V)

in which
$R^3$, $R^4$ and $R^6$ are as defined above with compounds of the general formula (VI)

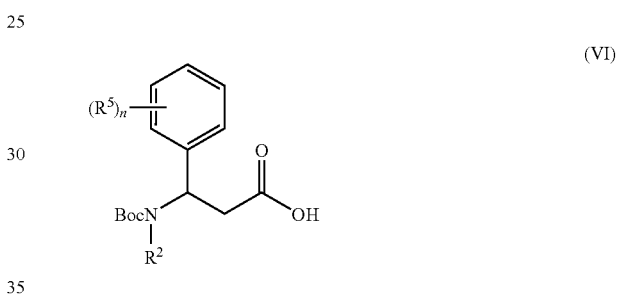

(VI)

in which
$R^2$, $R^5$ and n are as defined above, it being possible for these to be present where appropriate in activated form.

Suitable agents for converting the compounds into the activated form are, for example, carbodiimides such as N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic acid anhydride, or isobutyl chloroformate, or bis(2-oxo-3-oxazolidinyl)phosphoryl chloride or benzotriazolyl-oxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-aza-benzotriazol-1-yl)-N,N,N',N'-tetramethyluronium hexafluorophosphate (HATU), or 1-hydroxybenzotriazole (HOBt), or benzotriazol-1-yloxytris(dimethylamino)-phosphonium hexafluorophosphate (BOP), or mixtures thereof with bases.

Examples of bases include alkali metal carbonates, such as sodium or potassium carbonate, or sodium or potassium hydrogencarbonate, or organic bases such as trialkylamines, e.g., triethylamine, N-methylmorpholine, N-methylpiperidine, 4-dimethylaminopyridine or diisopropylethylamine.

Preference is given to using HATU and diisopropylethylamine.

Suitable solvents here are inert organic solvents which do not change under the reaction conditions. They include halogenated hydrocarbons such as dichloromethane or trichloromethane, hydrocarbons such as benzene, xylene, toluene, hexane, cyclohexane, or petroleum fractions, nitromethane, dimethylformamide or acetonitrile, or ethers such as diethyl ether, tetrahydrofuran or dioxane. It is also possible to use mixtures of the solvents. Particular preference is given to a mixture of dichloromethane and dimethylformamide.

The compounds of the general formula (V) are known from the literature or are new and can be prepared by adding acid, particularly hydrochloric acid or trifluoroacetic acid, to compounds of the general formula (VII)

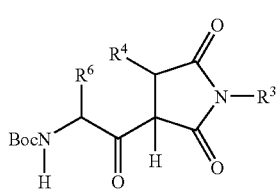

(VII)

in which
$R^3$, $R^4$ and $R^6$ are as defined above.

Suitable solvents here are inert organic solvents which do not change under the reaction conditions. They include halogenated hydrocarbons such as dichloromethane or trichloromethane, hydrocarbons such as benzene, xylene, toluene, hexane, cyclohexane, or petroleum fractions, nitromethane, dimethylformamide or acetonitrile, or ethers such as diethyl ether, tetrahydrofuran or dioxane. It is also possible to use mixtures of the solvents. Particular preference is given to using hydrochloric acid in dioxane or trifluoroacetic acid in dichloromethane.

The compounds of the general formula (VI) are known or can be prepared according to instructions known from the literature. (Regarding the preparation of aromatic beta-amino acids see: S. Rault, P. Dallemagne, M. Robba, *Bull Soc. Chim. Fr.*, 1987, 1079-1083).

The compounds of the general formula (VII) are known or can be prepared by methods known from the literature. (Cf., e.g., S. G. Davies, D. J. Dixon, *J. Chem. Soc., Perkin Trans.* 1, 1998, 17, 2635-2643.)

The compounds of the general formula (III) are known or can be prepared by methods known from the literature.

The compounds of the general formula (IIIb), (IIIc) und (IIId) are known or can be prepared by methods known from the literature.

In the general formulae (VI) and (VII) the Boc group can also be replaced by other amino acid protecting groups, such as fluorenylmethoxycarbonyl (Fmoc) or benzyloxycarbonyl, for example, which can be eliminated by standard methods (Greene, T. W., Wuts, G. M., Protective Groups in Organic Synthesis, 3rd ed., Wiley 1999).

The reactions described above take place in general in a temperature range from −78° C. up to reflux temperature, preferably from −78° C. to +20° C.

The reactions can be conducted under normal, elevated or reduced pressure (e.g., from 0.5 to 5 bar). They are generally performed under atmospheric pressure.

The flow diagrams below are intended to illustrate the processes:

Scheme 1:

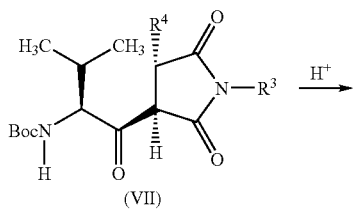

(VII)

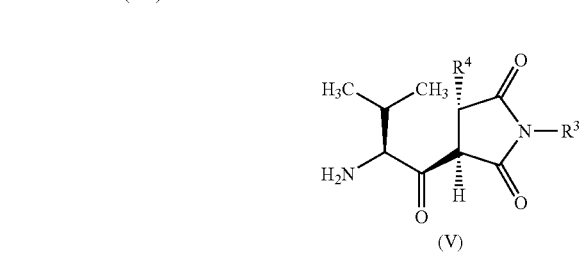

(V)

(V) +

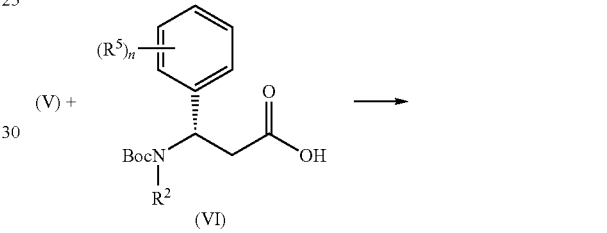

(VI)

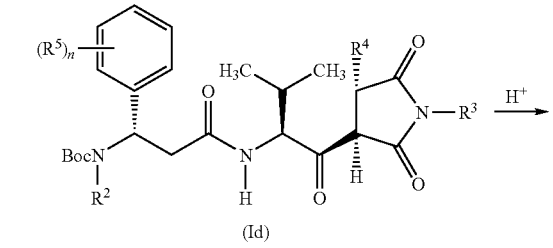

(Id)

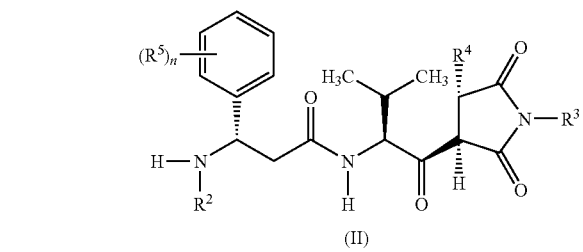

(II)

(II) + $R^{1-2}$—N═C═O (IIIa)

or (II) + $R^{1-2}R^{1-3}N$ 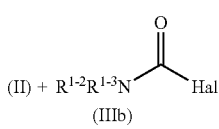 Hal (IIIb)

-continued

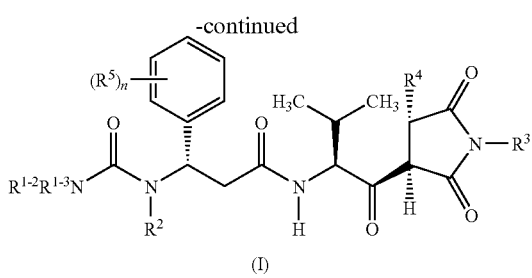

Scheme 2:

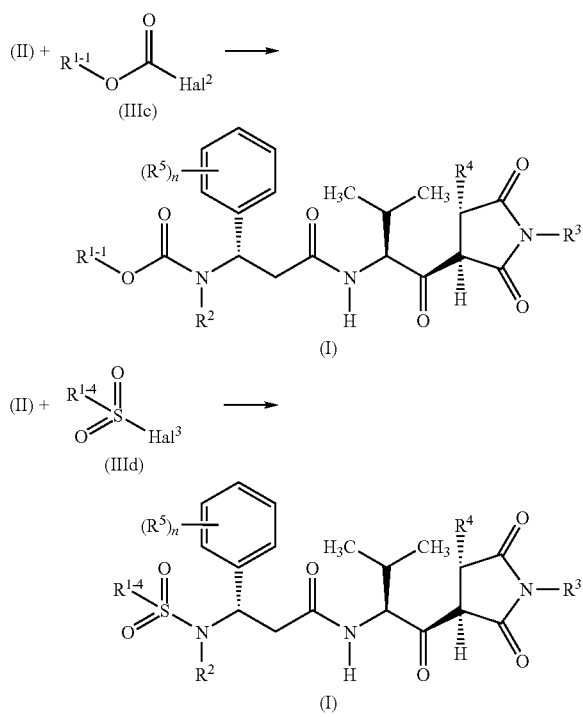

The present invention further relates to compounds of the general formula (I) for fighting diseases, particularly bacterial diseases, and to medicinal products comprising compounds of the general formula (I) and excipients, and also to the use of compounds of the general formula (I) for producing a medicinal product for treating bacterial diseases.

The formulations of the invention are particularly active against bacteria and bacterialike microorganisms. They are therefore particularly suitable for the prophylaxis and chemotherapy of local and systemic infections in human and animal medicine that are induced by these pathogens.

By way of example it is possible to treat and/or prevent local and/or systemic diseases caused by the following pathogens or by combinations of the following pathogens:

Gram-positive cocci, e.g. staphylococci (*Staph. aureus, Staph. epidermidis*), enterococci (*E. faecalis, E. faecius*) and streptococci (*Strept. agalactiae, Strept. pneumoniae*); gram-negative cocci (*Neisseria gonorrhoeae*) and gram-negative rods such as enterobacteria, e.g., *Escherichia coli, Haemophilus influenzae, Citrobacter* (*Citrob. freundii, Citrob. divernis*), *Salmonella* and *Shigella*; and also *Klebsiellas* (*Klebs. pneumoniae, Klebs. oxytocy*), *Enterobacter* (*Ent. aerogenes, Ent. agglomerans*), *Haffia, Serratia* (*Serr. marcescens*), *Providencia, Yersinia*, and also the genus *Acinetobacter*. The antibacterial spectrum further embraces strictly anaerobic bacteria such as *Bacteroides fragilis*, representatives of the genus *Peptococcus, Peptostreptococcus*, and the genus *Clostridium*; and also *Mycoplasmas* (*M. pneumoniae, M. hominis, M. urealyticum*) and *Mycobacteria*, e.g., *Mycobacterium tuberculosis*.

The above listing of pathogens should be interpreted merely as exemplary and in no way as restrictive. Examples that may be mentioned of diseases which may be caused by the stated pathogens or combination infections and which may be prevented, remedied or cured by the preparations of the invention include the following:

Infectious diseases in humans, such as septic infections, bone and joint infections, skin infections, postoperative wound infections, abscesses, phlegmons, wound infections, infected burns, burn wounds, infections in the oral region, infections following dental operations, septic arthritis, mastitis, tonsillitis, genital infections and eye infections.

As well as in humans, bacterial infections in other species too can be treated.

Examples that may be mentioned include the following:

pigs: coli diarrhoea, enterotoxamia, sepsis, dysentery, salmonellosis, metritis-mastitis-agalactia syndrome, mastitis;

ruminants (cattle, sheep, goats): diarrhoea, sepsis, bronchopneumonia, salmonellosis, pasteurellosis, mycoplasmosis, genital infections;

horses: bronchopneumonias, joint ill, puerperal and postpartum infections, salmonellosis;

dogs and cats: bronchopneumonia, diarrhoea, dermatitis, otitis, urinary tract infections, prostatitis;

poultry (chickens, turkeys, quails, pigeons, ornamental birds and others):

mycoplasmosis, *E. coli* infections, chronic respiratory tract diseases, salmonellosis, pasteurellosis, *psittacosis*.

It is also possible to treat bacterial diseases associated with the breeding and keeping of farmed and ornamental fish, in which case the antibacterial spectrum extends beyond the aforementioned pathogens to embrace further pathogens such as *Pasteurella, Brucella, Campylobacter, Listeria, Erysipelothris, Corynebacteria, Borellia, Treponema, Nocardia, Rickettsia*, and *Yersinia*, for example.

The active ingredient may act systemically and/or locally. For that purpose it can be administered in appropriate manner, such as orally, parenterally, pulmonically, nasally, sublingually, lingually, buccally, rectally, transdermally, conjunctivally, otically or as an implant.

For these administration routes the active ingredient can be administered in suitable administration forms.

Administration forms suitable for oral administration are known such forms which deliver the active ingredient rapidly and/or in a modified way, such as tablets (uncoated and coated tablets, such as film-coated tablets or tablets provided with enteric coatings), capsules, sugar-coated tablets, granules, pellets, powders, emulsions, suspensions, and solutions, for example.

Parenteral adminstration can be made with avoidance of an absorption step (intravenously, intraarterially, intracardially, intraspinally or intralumbarly) or with inclusion of absorption (intramuscularly, subcutaneously, intracutaneously, percutaneously, or intraperitoneally). Administration forms suitable for parenteral administration include preparations for injection and infusion in the form of solutions, suspensions, emulsions, lyophilizates, and sterile powders.

Preference is given to parenteral administration, more particularly intravenous administration.

Examples suitable for the other administration routes are pharmaceutical forms for inhalation (including powder inhalers, nebulizers), nasal drops/solutions, sprays; capsules or tablets to be administered lingually, sublingually or buccally, suppositories, ear and eye preparations, vaginal capsules, aqueous suspensions (lotions, shaking mixtures), lipophilic suspensions, ointments, creams, milk, pastes, dusting powders or implants.

The active ingredients can be converted in conventional manner into the stated administration forms. This is done with the use of inert, nontoxic, pharmaceutically appropriate excipients. These include, among others, carriers (e.g. microcrystalline cellulose), solvents (e.g., liquid polyethylene glycols), emulsifiers (e.g., sodium dodecyl sulfate), dispersants (e.g., polyvinylpyrrolidone), synthetic and natural biopolymers (e.g., albumen), stabilizers (e.g., antioxidants such as ascorbic acid), colorants (e.g., inorganic pigments such as iron oxides) or flavor and/or odor masking agents.

It has generally proven advantageous in the case of parenteral administration to administer amounts of about 5 to 250 mg/kg body weight per 24 hours in order to achieve effective results. In the case of oral administration the amount is about 5 to 100 mg/kg body weight per 24 hours.

It may nevertheless be necessary, where appropriate, to deviate from the amounts specified, specifically as a function of body weight, administration route, individual response to the active ingredient, type of preparation, and time of interval at which administration takes place.

A. EVALUATION OF PHYSIOLOGICAL ACTIVITY

Determination of Minimum Inhibitory Concentration (MIC):

The MIC is determined in the liquid dilution test. Overnight cultures of the test organisms are diluted to a cell count of $10^5$ organisms per ml in Isosensitest medium (manufacturer: Difco) and are incubated with dilutions of the test substances (1:2 dilution states). Exceptions are the tests with *S. pneumoniae* G9A, which are conducted in BHI broth (Difco) plus 20% bovine serum, and with *H. influenzae*, which are conducted in BHI broth (Difco) plus 20% bovine serum, 10 μg/ml hemin and 1% Isovitale (Becton Dickinson).

The cultures are incubated at 37° C. for 18-24 hours; *S. pneumoniae* and *H. influenzae* in the presence of 8-10% $CO_2$.

Results:

The lowest concentration of each substance at which there was no longer any visible bacterial growth is defined as the MIC. The MICs in μmol/l of some compounds according to the invention against a series of test organisms are listed by way of example in the table below.

| Ex. | *Staphylococcus aureus* 133 | *Haemophilus influenzae* Spain 7 |
| --- | --- | --- |
| 2 | 3.9 | 62.5 |
| 5 | 62.5 | n.d.* |
| 6 | 62.5 | 62.5 |
| 7 | 15.6 | 31.3 |
| 9 | 7.8 | 62.5 |
| 10 | 7.8 | 125 |
| 33 | 31.3 | 125 |
| 35 | 0.98 | 62.5 |
| 47 | 7.8 | 125 |

*n.d.: not determined

Systemic Infection with *S. aureus* 133

*S. aureus* 133 cells are cultured overnight in BH broth (Oxoid). The overnight culture is diluted 1:100 in fresh BH broth and spun at high speed for 3 hours. The bacteria in the logarithmic growth phase are centrifuged off and washed 2× with buffered physiological saline solution. Subsequently a photometer (Dr. Lange LP 2W) is used to establish a cell suspension in saline solution with an extinction of 50 units. Following a dilution step (1:15) this suspension is mixed 1:1 with a 10% mucin suspension. 0.25 ml/20 g mouse of this infection solution is administered intraperitoneally. This corresponds to a cell count of approximately $1 \times 10E^6$ organisms/mouse. The intraperitoneal or intravenous therapy is practised 30 minutes following infection. Female CFW1 mice are used for the infection experiment. The survival of the animals is recorded over 6 days.

B. EXAMPLES

Abbreviations:

Boc tert-butoxycarbonyl $CDCl_3$ deuterochloroform

DIEA N,N-diisopropylethylamine

DMSO dimethyl sulfoxide

EDC N'-(3-dimethylaminopropyl)-N-ethylcarbodiimide×HCl eq. equivalent

ESI electrospray ionization (for MS)

Fmoc fluorenylmethoxycarbonyl

HATU O-(7-azabenzotriazol-1-yl)-N,N,N',N'-tetramethyluronium hexafluorophosphate h hour HOBt 1-hydroxy-1H-benzotriazole×$H_2O$ HPLC high-pressure, high-performance liquid chromatography LC-MS liquid chromatography-coupled mass spectroscopy MS mass spectroscopy NMR nuclear magnetic resonance spectroscopy PS-DIEA N,N-diisopropylethylamine-polystyrene (resin)

$R_f$ retention index (for TLC)

RP-HPLC reverse phase HPLC

RT room temperature $R_t$ retention time (for HPLC).

HPLC and LC-MS Methods:

Method 1:

Column: Kromasil C18, L-R temperature: 30° C., flow rate=0.75 ml min$^{-1}$, mobile phase: A=0.01 M $HClO_4$, B=acetonitrile, gradient:→0.5 min 98% A→4.5 min 10% A→6.5 min 10% A.

Method 2:

Column: Kromasil C18 60*2, L-R temperature: 30° C., flow rate=0.75 ml min$^{-1}$, mobile phase: A=0.01 M $H_3PO_4$, B=acetonitrile, gradient:→0.5 min 90% A→4.5 min 10% A→6.5 min 10% A.

Method 3:

Column: Kromasil C18 60*2, L-R temperature: 30° C., flow rate=0.75 ml min$^{-1}$, mobile phase: A=0.005 M HClO$_4$, B=acetonitrile, gradient:→0.5 min 98% A→4.5 min 10% A→6.5 min 10% A.

Method 4:

Column: Symmetry C18 2.1×150 mm, column oven: 50° C., flow rate=0.6 ml min$^{-1}$, mobile phase: A=0.6 g 30% HCl/l water, B=acetonitrile, gradient: 0.0 min 90% A→4.0 min 10% A→9 min 10% A.

Method 5:

Instrument: Micromass Quattro LCZ; column: Symmetry C18, 50 mm×2.1 mm, 3.5 µm, temperature: 40° C., flow rate=0.5 ml min$^{-1}$, mobile phase A=acetonitrile+0.1% formic acid, mobile phase B=water+0.1% formic acid, gradient: 0.0 min 10% A→4 min 90% A→6 min 90% A.

Method 6:

Instrument: Micromass Platform LCZ; column Symmetry C18, 50 mm×2.1 mm, 3.5 µm, temperature: 40° C., flow rate=0.5 ml min$^{-1}$, mobile phase A=acetonitrile+0.1% formic acid, mobile phase B=water+0.1% formic acid, gradient: 0.0 min 10% A→4 min 90% A→6 min 90% A.

Method 7:

Instrument: Micromass Quattro LCZ; column Symmetry C18, 50 mm×2.1 mm, 3.5 µm, temperature: 40° C., flow rate=0.5 ml min$^{-1}$, mobile phase A=acetonitrile+0.1% formic acid, mobile phase B=water+0.1% formic acid, gradient: 0.0 min 5% A→1 min 5% A→5 min 90% A→6 min 90% A.

Method 8:

Instrument: Finnigan MAT 900S; column: Symmetry C 18, 150 mm×2.1 mm, 5.0 µm; mobile phase B: water+0.3 g 35% HCl, mobile phase A: acetonitrile; gradient: 0.0 min 2% A→2.5 min 95% A→5 min 95% A; oven: 70° C., flow rate: 1.2 ml/min.

Method 9:

Column: Symmetry C18 3.9 mm×150 mm, column oven: 40° C., flow rate=1.5 ml min$^{-1}$, mobile phase: A=water+0.05% H$_3$PO$_4$, B=acetonitrile, gradient: 0.0 min 10% B→0.6 min 10% B→3.8 min 100% B→5.0 min 100% B.

Method 10:

Instrument: Waters Alliance 2790 LC; column: Symmetry C18, 50 mm×2.1 mm, 3.5 µm; mobile phase A: water+0.1% formic acid, mobile phase B: acetonitrile+0.1% formic acid; gradient: 0.0 min 5% B→5.0 min 10% B→6.0 min 10% B; temperature: 50° C., flow rate: 1.0 ml/min, UV detection: 210 nm.

Method 11:

Instrument type MS: Micromass ZQ; instrument type HPLC: Waters Alliance 2790; column: Symmetry C 18, 50 mm×2.1 mm, 3.5 µm; mobile phase B: acetonitrile+0.05% formic acid, mobile phase A: water+0.05% formic acid; gradient: 0.0 min 10% B→3.5 min 90% B→5.5 min 90% B; oven: 50° C., flow rate: 0.8 ml/min, UV detection: 210 nm.

Method 12:

Instrument: Waters Alliance 2790 LC; column: Symmetry C18, 50 mm×2.1 mm, 3.5 µm; mobile phase A: water+0.05% formic acid, mobile phase B: acetonitrile+0.05% formic acid; gradient: 0.0 min 5% B→4.5 min 10% B→4.5 min 10% B; temperature: 50° C., flow rate: 1.0 ml/min, UV detection: 210 nm.

Method 13:

Instrument: Micromass Quattro LCZ, HP1100; column: Symmetry C18, 50 mm×2.1 mm, 3.5 µm; mobile phase A: water+0.05% formic acid, mobile phase B: acetonitrile+0.05% formic acid; gradient: 0.0 min 90% A→4.0 min 10% A→6.0 min 10% A; oven: 40° C., flow rate: 0.5 ml/min, UV detection: 208-400 nm.

Method 14:

Instrument: Micromass Platform LCZ, HP1100; column: Symmetry C18, 50 mm×2.1 mm, 3.5 µm; mobile phase A: water+0.05% formic acid, mobile phase B: acetonitrile+0.05% formic acid; gradient: 0.0 min 90% A→4.0 min 10% A→6.0 min 10% A; oven: 40° C., flow rate: 0.5 ml/min, UV detection: 208-400 nm.

Method 15:

Instrument: Waters Alliance 2790 LC; column: Symmetry C18, 50 mm×2.1 mm, 3.5 µm; mobile phase A: water+0.05% formic acid, mobile phase B: acetonitrile+0.05% formic acid; gradient: 0.0 min 10% B→4.0 min 90% B→6.0 min 90% B; temperature: 50° C., flow rate: 0.0 min 0.5 ml/min→4.0 min 0.8 ml/min, UV detection: 210 nm.

Method 16:

Instrument type MS: Micromass ZQ; instrument type HPLC: Waters Alliance 2790; column: Symmetry C 18, 50 mm×2.1 mm, 3.5 µm; mobile phase B: acetonitrile+0.05% formic acid, mobile phase A: water+0.05% formic acid; gradient: 0.0 min 5% B 4.5 min 90% B 5.5 min 90% B; oven: 50° C., flow rate: 1.0 ml/, UV detection: 210 nm.

Method 17:

Instrument type MS: Micromass. ZQ; instrument type HPLC: Waters Alliance 2790; column: Uptisphere C 18, 50 mm×2.0 mm, 3.0 µm; mobile phase B: acetonitrile+0.05% formic acid, mobile phase A: water+0.05% formic acid; gradient: 0.0 min 5% B→2.0 min 40% B→4.5 min 90% B→5.5 min 90% B; oven: 45° C., flow rate: 0.0 min 0.75 ml/min→4.5 min 0.75 ml/min→5.5 min 1.25 ml/min, UV detection: 210 nm.

Starting Compounds

Example 1A (3R,4S)-3-[(2S)-2-Amino-3-methylbutanoyl]-4-methyl-2,5-pyrrolidinedione hydrochloride

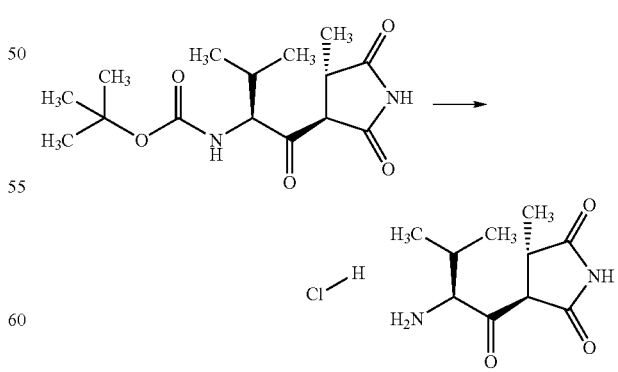

A solution cooled at 0° C. of 4.40 g (14.09 mmol) of (3R,4S)-3-[(2S)-2-(tert-butoxycarbonyl)amino-3-methylbutanoyl]-4-methyl-2,5-pyrrolidinedione (preparation: S. G. Davies, D. J. Dixon, *J. Chem. Soc., Perkin Trans.* 1, 1998, 17, 2635-2643) in 20 ml of dioxane is admixed dropwise with 35 ml of 4N hydrochloric acid solution in 1,4-dioxane. When the addition has been made the mixture is warmed to room temperature and stirred for 2 h, before being concentrated in vacuo. The residue is treated with diethyl ether. The precipitated crystals are filtered off and dried under a high vacuum. Yield: 2.99 g of colorless crystals (86% of theory).

MS (ESI+): m/z (%)=213 (M+H$^+$) (100).

HPLC (method 4): R$_t$=0.41 min.

General Procedure A

Acylation of (3R,4S)-3-[(2S)-2-amino-3-methylbutanoyl]-4-methyl-2,5-pyrrolidinedione hydrochloride with carboxylic acid derivatives

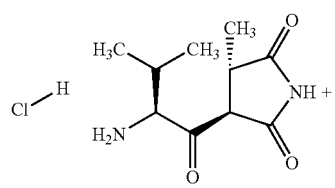

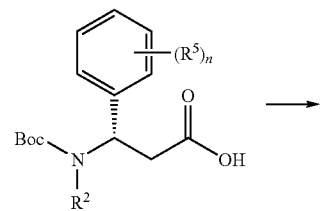

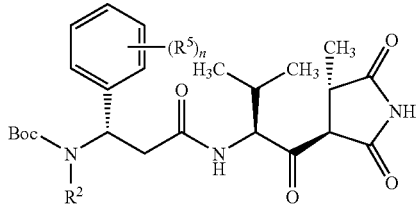

A solution of (3R,4S)-3-[(2S)-2-amino-3-methylbutanoyl]-4-methyl-2,5-pyrrolidine-dione hydrochloride (1.0 eq.) in a mixture (about 5:1) of absolute dichloromethane and N,N-dimethylformamide (about 0.2 to 0.35 mol/l) is admixed with about 1.2 to 1.4 eq. of N-blocked β-amino acid derivative. The mixture is cooled to 0° C. and admixed with 1.2 to 1.4 eq. of HATU. 2.3 to 2.6 eq. of diisopropylethylamine are added dropwise over 30 minutes. When the addition has been made the reaction mixture is stirred at room temperature for 3 to 5 h, before being concentrated in vacuo. The product can be obtained by chromatography on silica gel [mobile phases: mixtures of cyclohexane/ethyl acetate (about 1:2) or mixtures of dichloromethane and ethanol (about 98:2)] or by RP-HPLC (mobile phases: variable gradients of water and acetonitrile) or, alternatively, by a combination of both methods.

Example 2A tert-Butyl ((S)-2-{(S)-2-methyl-1-[1-((3R,4S)-4-methyl-2,5-dioxopyrrolidin-3-yl)-methanoyl]propyl-carbamoyl}-1-phenylethyl)carbamate

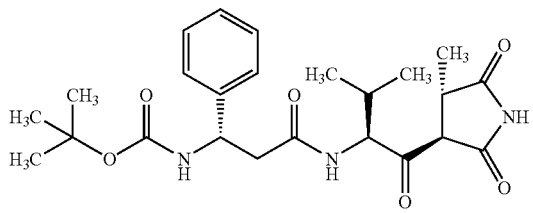

$^1$H NMR (400 MHz, d$_6$-DMSO): δ=11.45 (s, 1H), 7.98 (d, 1H), 7.31-7.24 (m, 5H), 7.20 (br. s, 1H), 4.88-4.82 (br. s, 1H), 4.69 (br. s, 1H), 3.98 (d, 1H), 2.95-2.89 (m, 1H), 2.77-2.69 (m, 1H), 2.51-2.44 (m, 1H), 2.35-2.29 (m, 1H), 1.10 (d, 3H), 0.85 (d, 3H), 0.78 (d, 3H).

MS (ESI+): m/z (%)=460 (M+H$^+$) (100).

HPLC (method 6): R$_t$=3.90 min.

General Procedure B

Deblocking of Boc-protected derivatives

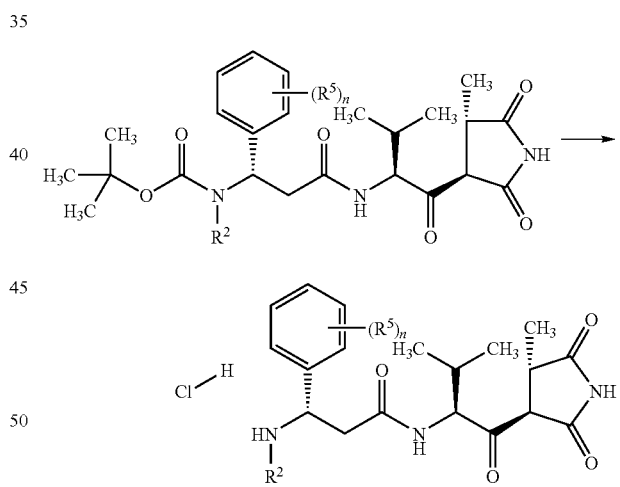

A mixture cooled at 0° C. of tert-butoxycarbonyl (BOC) protected amine derivative in 1,4-dioxane (about 0.5 to 1.0 mol/l) is admixed dropwise over 30 minutes with 3-5 eq of 4N hydrochloric acid solution in 1,4-dioxane. When the addition has been made the mixture is warmed to room temperature and stirred for about 2 to 3 h, before being concentrated in vacuo. The residue is treated with a mixture of dichloromethane and diethyl ether (about 1:2). The precipitated crystals are filtered off with suction and dried under a high vacuum. The product is obtained in the form of the hydrochloride.

Example 3A (S)-3-Amino-{(s)-2-methyl-1-[1-((3R,4S)-4-methyl-2,5-dioxopyrrolidin-3-yl)-methanoyl]propyl}-3-phenylpropionamide hydrochloride

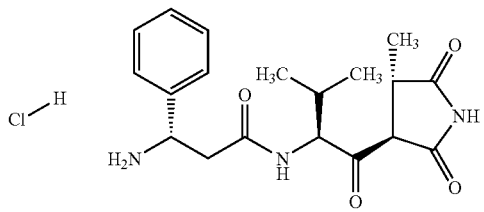

¹H NMR (200 MHz, d₆-DMSO): δ=11.49 (br. s, 1H), 8.5 (br. s, about 3H), 7.54-7.32 (m, 5H), 4.69-4.55 (m, 2H), 3.89 (d, 1H), 3.06-2.80 (m, 3H), 2.39-2.25 (m, 1H), 1.01 (d, 3H), 0.81 (d, 3H), 0.75 (d, 3H).

MS (ESI+): m/z (%)=360 (M–Cl)⁺(100).

HPLC (method 4): $R_t$=1.44 min.

In analogy to Example 1A, from the corresponding tert-butoxycarbonylamino derivatives, by treatment with hydrochloric acid in dioxane, it is possible to prepare the following amines in the form of their hydrochlorides and to react them further directly:

| Example | Structure | MW |
|---|---|---|
| 4A | ![structure] | 238.29 |
| 5A | ![structure] | 240.30 |

General Procedure E

Preparation of N-tert-butoxycarbonyl-protected beta-amino acids

The beta-amino acid (1 eq.) [synthesized by procedures known from the literature (e.g., S. Rault, P. Dallemagne, M. Robba, *Bull. Soc. Chim. Fr.,* 1987, 1079-1083; L. Lázár, T. Martinek, G. Bernáth, F. Fülöp, *Synth. Comm.,* 1998, 28, 219-224)] is introduced in water (concentration about 0.3-1 mol/l), and triethylamine (1.5-3 eq.) is added. Then a solution of 2-(tert-butoxycarbonyloximino)phenylacetonitrile (1.1 eq.) in dioxane (0.3-1 mol/l) is added. The reaction mixture is stirred at room temperature for 3 h, diluted with water and washed with diethyl ether. The aqueous phase is acidified with 5% strength citric acid (about pH 2) and extracted three times with ethyl acetate. The combined organic phases are washed with saturated sodium chloride solution, dried over sodium sulfate, filtered and concentrated. The crude product can if desired be recrystallized from ethyl acetate/n-hexane.

General procedure E can be used to give the following compounds:

| Example | Structure | MW | MS | HPLC |
|---|---|---|---|---|
| 6A | ![structure] | 310.3 | MS (ES+), m/z (%): 311 (M + H)⁺ | HPLC (method 8): $R_t$ = 3.87 min |

-continued

| Example | Structure | MW | MS | HPLC |
|---|---|---|---|---|
| 7A | 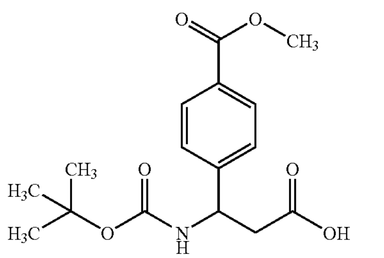 | 323.34 | MS (ES+), m/z (%): 324 (M + H)+ | HPLC (method 8): $R_t$ = 2.39 min |
| 8A | 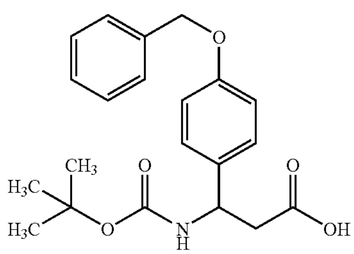 | 371.44 | MS (ES+), m/z (%): 372 (M + H)+ | HPLC (method 9): $R_t$ = 4.47 min |
| 9A | 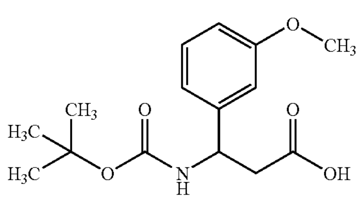 | 295.34 | MS (ES+), m/z (%): 296 (M + H)+ | |
| 10A | 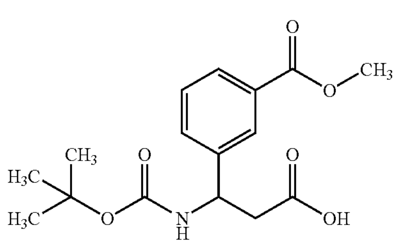 | 323.35 | | HPLC (method 9): $R_t$ = 3.96 min |

General Procedure F

Reaction of (3S)-1-(benzyloxy)-3-methyl-2,5-pyrrolidinedione with activated N-(tert-butoxycarbonyl) amino acids The N-(tert-butoxycarbonyl) amino acid is introduced in tetrahydrofuran (about 0.3-1 mol/l), and 1.1 eq of N,N-carbonyldiimidazole are added. The mixture is stirred at room temperature for 2 h. Then 1 eq of (3S)-1-(benzyloxy)-3-methyl-2,5-pyrrolidinedione (preparation: S. G. Davies, D. J. Dixon, *J. Chem. Soc., Perkin Trans.* 1, 1998, 17, 2635-2643) is added and the entire mixture is introduced dropwise over the course of 30 minutes into a 1 molar solution cooled to −65° C. of lithium hexamethyldisilazide (2 eq) in tetrahydrofuran. When the addition has been made stirring is continued at −65° C. for 15 minutes, before saturated aqueous ammonium chloride solution is added. The organic phase is dried over magnesium sulfate, filtered and concentrated. The crude product is purified by RP-HPLC (mobile phase: water-acetonitrile, gradient).

General procedure F can be used to give the following compounds:

| Example | Structure | MW | MS | HPLC |
|---|---|---|---|---|
| 11A | 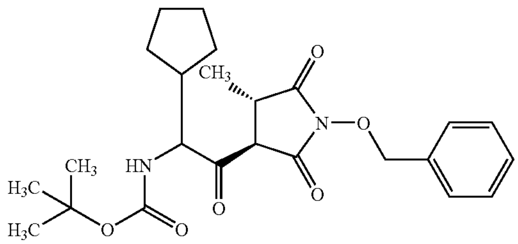 | 444.53 | MS (ES−), m/z (%): 443 (M − H)−(100) | HPLC (method 12): $R_t$ = 3.97 min |
| 12A | 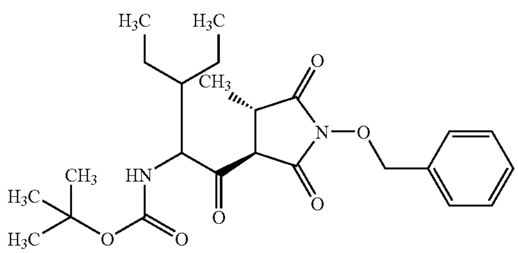 | 446.54 | MS (ES−), m/z (%): 445 (M − H)−(100) | HPLC (method 17): $R_t$ = 4.40 min |

General Procedure G

Reductive deprotection of 1-benzyloxy-2,5-pyrrolidinediones

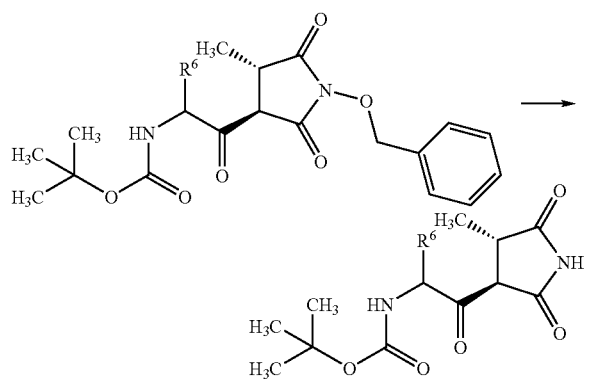

Deprotection takes place in analogy to S. G. Davies, D. J. Dixon, *J. Chem. Soc., Perkin Trans.* 1, 1998, 17, 2635-2643.

The 1-benzyloxy-2,5-pyrrolidinedione (1 eq) is dissolved in methanol (about 0.02 mol/l), admixed with a catalytic amount of palladium on carbon (10%) and stirred under a hydrogen atmosphere (atmospheric pressure) for 1 h. The reaction mixture is then filtered and concentrated. The residue is dissolved in acetonitrile (about 0.05 mol/l) and added dropwise to a solution of 2-bromoacetophenone (1 eq) in acetonitrile (about 0.03 mol/l) at room temperature. Thereafter 1.5 eq. of triethylamine in acetonitrile (about 0.35 mol/l) are added dropwise to the reaction mixture over a period of 2 h. The reaction mixture is stirred overnight at room temperature and concentrated and the crude product is purified by RP-HPLC (mobile phase: acetonitrile/water+0.3 ml of 37% hydrochloric acid/l, gradient).

General procedure G can be used to give the following compounds:

| Example | Structure | MW | MS | HPLC |
|---|---|---|---|---|
| 13A | 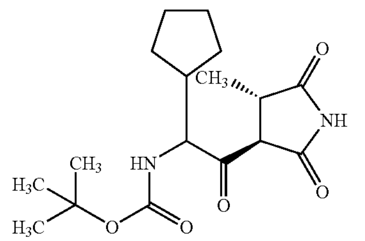 | 338.40 | MS (ES−), m/z (%): 337 (M − H)⁻(100) | HPLC (method 13): $R_t$ = 4.16 min |
| 14A | 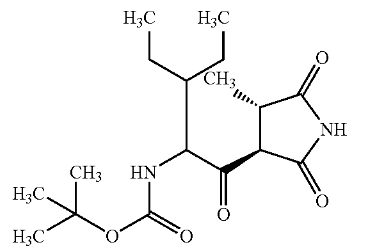 | 340.42 | MS (ES−), m/z (%): 339 (M − H)⁻(100) | HPLC (method 17): $R_t$ = 3.59 min |

Preparation Examples

General Procedure C

Preparation of urea derivatives starting from substituted (3R,4S)-3-[(2S)-2-amino-3-methylbutanoyl]-4-methyl-2,5-pyrrolidinedione derivatives (in the form of their hydrochlorides) and isocyanates

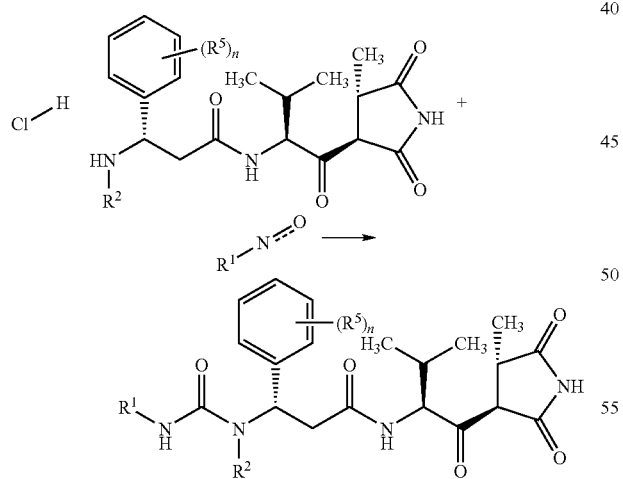

A mixture of hydrochloride (1.0 eq.) in absolute dichloroethane (about 0.1 mol/l, with optional addition of small amounts of N,N-dimethylformamide) is admixed at room temperature with about 1.5 eq. of polymer-bound amine base (PS-DIEA from Argonaut Technologies, loading: about 3.8 mmol/g resin) and isocyanate (about 1-1.2 eq.). The mixture is shaken at room temperature overnight and filtered. The filtrate is applied to a silica gel cartridge. The product can be eluted with mixtures of dichloromethane and methanol (typically 95:5). Further purification by RP-HPLC is possible where appropriate.

Alternatively the amine hydrochloride and triethylamine (1 eq.) in tetrahydrofuran (about 0.1 mol/l) can be introduced and admixed with the isocyanate, dissolved in a little tetrahydrofuran, at room temperature. In this case the reaction mixture is stirred overnight, then diluted with dichloromethane and washed with water. The organic phase is dried over magnesium sulfate, filtered and concentrated. The crude product can be purified by RP-HPLC (mobile phase: water/acetonitrile, gradient).

Example 1

(S)-3-(3-Butylureido)-N-{(S)-2-methyl-1-[1-((3R,4S)-4-methyl-2,5-dioxopyrrolidin-3-yl)-methanoyl]propyl}-3-phenylpropionamide

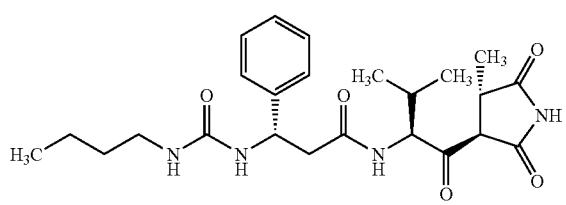

¹H NMR (400 MHz, $d_6$-DMSO): δ=11.35 (s, 1H), 8.10 (d, 1H), 7.30-7.16 (m, 6H), 6.43 (d, 1H), 6.05 (t, 1H), 5.09-5.01 (m, 1H), 4.53 (dd, 1H), 3.92 (d, 1H), 2.98-2.90 (m, about 1H), 2.78 (dd, 1H), 2.56 (dd, 1H), 2.28-2.23 (m, 1H), 1.35-1.20 (m, 6H), 1.10 (d, 3H), 0.85 (t, 3H), 0.75 (d, 3H), 0.70 (d, 3H).

MS (ESI+): m/z (%)=459 (M+H⁺) (100).

HPLC (method 4): $R_t$=2.22 min.

Example 2

(S)-3-(3-Benzylureido)-N-{(S)-2-methyl-1-[1-((3R,4S)-4-methyl-2,5-dioxopyrrolidin-3-yl)-methanoyl]propyl}-3-phenylpropionamide

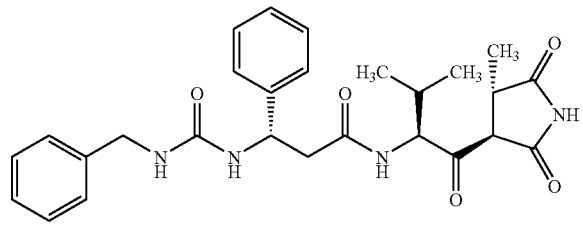

MS (ESI+): m/z (%)=493 (M+H$^+$) (100).
HPLC (method 4): R$_t$=2.28 min.

Example 3

(S)-3-(3-Allylureido)-N-{(S)-2-methyl-1-[1-((3R,4S)-4-methyl-2,5-dioxopyrrolidin-3-yl)-methanoyl]propyl}-3-phenylpropionamide

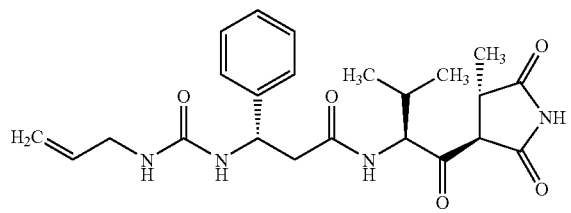

MS (ESI+): m/z (%)=443 (M+H$^+$) (100).
HPLC (method 5): R$_t$=3.23 min.

Example 4

(S)-3-(3-Biphenyl-4-ylureido)-N-{(S)-2-methyl-1-[1-((3R,4S)-4-methyl-2,5-dioxo-pyrrolidin-3-yl)methanoyl]propyl}-3-phenylpropionamide

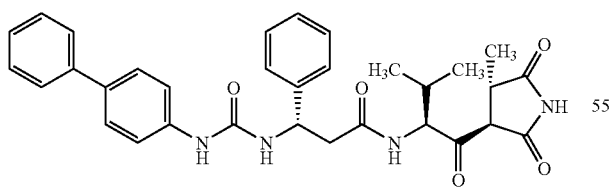

$^1$H NMR (400 MHz, d$_6$-DMSO): δ=11.32 (br s, 1H), 8.87 (s, 1H), 8.15 (d, 1H), 7.65-7.15 (m, 14H), 6.99 (d, 1H), 5.21-5.10 (m, 1H), 4.57 (dd, 1H), 3.94 (d, 1H), 2.95-2.85 (m, 2H), 2.74-2.63 (m, 1H), 2.31-2.18 (m, 1H), 1.10 (d, 3H), 0.72 (d, 3H), 0.65 (d, 3H).
MS (ESI+): m/z (%)=555 (M+H$^+$) (100).
HPLC (method 6): R$_t$=4.31 min.

Example 5

(S)-N-{(S)-2-Methyl-1-[1-((3R,4S)-4-methyl-2,5-dioxopyrrolidin-3-yl)-methanoyl]-propyl}-3-phenyl-3-(3-phenylureido)propionamide

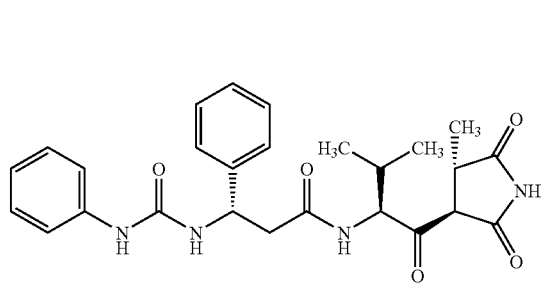

$^1$H NMR (400 MHz, d$_6$-DMSO): δ=11.32 (br s, 1H), 8.74 (s, 1H), 8.15 (d, 1H), 7.48-7.15 (m, 9H), 6.99-6.82 (m, 2H), 5.20-5.10 (m, 1H), 4.56 (dd, 1H), 3.95 (d, 1H), 2.95-2.85 (m, 2H), 2.72-2.62 (m, 1H), 2.29-2.18 (m, 1H), 1.10 (d, 3H), 0.71 (d, 3H), 0.68 (d, 3H).
MS (ESI+): m/z (%)=501 (M+Na$^+$) (100).
HPLC (method 5): R$_t$=3.71 min.

Example 6

(S)-3-[3-(4-Methoxyphenyl)ureido]-N-{(S)-2-methyl-1-[1-((3R,4S)-4-methyl-2,5-dioxopyrrolidin-3-yl)methanoyl]propyl}-3-phenylpropionamide

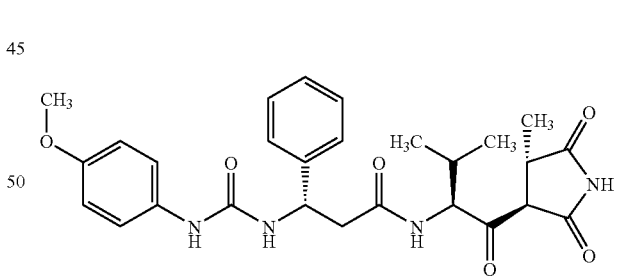

$^1$H NMR (400 MHz, d$_6$-DMSO): δ=11.35 (s, 1H), 8.55 (s, 1H), 8.16 (d, 1H), 7.33-7.18 (m, 7H), 6.88-6.75 (m, 3H), 5.18-5.10 (m, 1H), 4.57 (dd, 1H), 3.94 (d, 1H), 3.68 (s, 3H), 2.95-2.82 (m, 2H), 2.70-2.60 (m, 1H), 2.35-2.20 (m, 1H), 1.09 (d, 3H), 0.70 (d, 3H), 0.67 (d, 3H).
MS (ESI+): m/z (%)=509 (M+H$^+$) (55), 531 (M+Na$^+$) (100).
HPLC (method 5): R$_t$=3.59 min.

General Procedure D

Preparation of N-alkyl-substituted urea derivatives starting from substituted (3R,4S)-3-[(2S)₂-amino-3-methylbutanoyl]-4-methyl-2,5-pyrrolidinedione derivatives in the form of their hydrochlorides and chloro amine acid derivatives

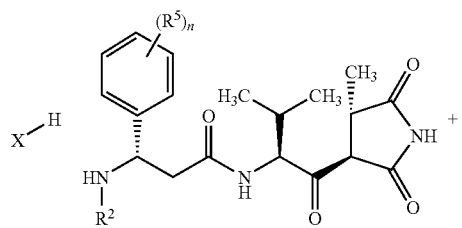

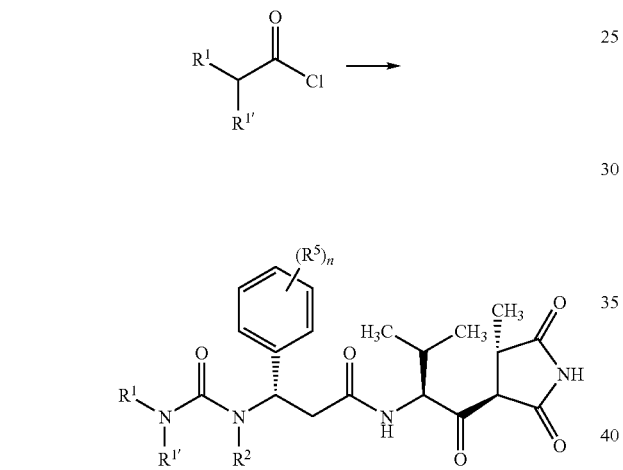

A mixture of hydrochloride (1.0 eq.) in absolute dichloroethane (about 0.1 mol/l) is admixed at room temperature with about 2.4 eq. of polymer-bound amine base (PS-DIEA from Argonaut Technologies, loading: about 3.8 mmol/g resin) and chloro amine acid derivative (about 1.2 eq.). The mixture is shaken at room temperature overnight and then filtered. The filtrate is applied to a silica gel cartridge. The product can be eluted with mixtures of dichloromethane and methanol (typically 95:5). Further purification by RP-HPLC is possible where appropriate.

Alternatively the amine hydrochloride and triethylamine (2 eq.) can be introduced in tetrahydrofuran (about 0.1 mol/l) and admixed with the chloro amine acid derivative, dissolved in a little tetrahydrofuran where appropriate, at room temperature. In this case the reaction mixture is stirred overnight and then concentrated at temperatures between room temperature and 40° C., admixed with dichloromethane and washed with water. The organic phase is dried over magnesium sulfate, filtered and concentrated. The crude product can be purified by RP-HPLC (mobile phase: water/acetonitrile, gradient).

Example 7

(S)-N-{(S)-2-Methyl-1-[1-((3R,4S)-4-methyl-2,5-dioxopyrrolidin-3-yl)methanoyl]-propyl}-3-(3-methyl-3-phenylureido)-3-phenylpropionamide

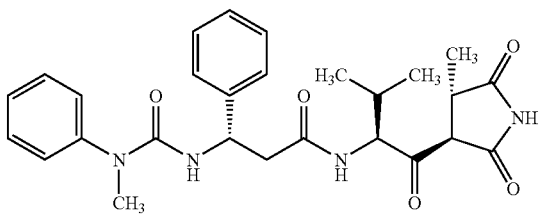

¹H NMR (400 MHz, d₆-DMSO): δ=11.35 (s, 1H), 8.10 (d, 1H), 7.40-7.15 (m, 10H), 6.59 (d, 1H), 5.13-5.08 (m, 1H), 4.59 (dd, 1H), 3.98 (d, 1H), 2.90 (dd, 1H), 2.82 (dd, 1H), 2.78-2.65 (m, 1H), 2.28-2.21 (m, 1H), 1.11 (d, 3H), 0.85 (t, 3H), 0.72 (d, 3H), 0.65 (d, 3H).

MS (ESI+): m/z (%)=493 (M+H⁺) (100).

HPLC (method 4): R_f=2.23 min.

Example 8

N-((S)-2-{(S)-2-Methyl-1-[1-((3R,4S)-4-methyl-2,5-dioxopyrrolidin-3-yl)-methanoyl]propylcarbamoyl}-1-phenylethyl)morpholine-4-carboxamide

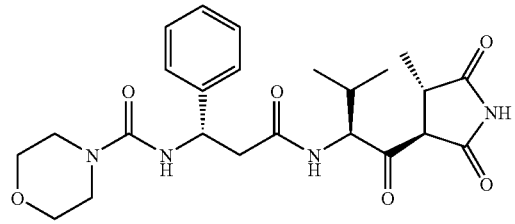

¹H NMR (400 MHz, d₆-DMSO): δ=11.30 (br. s, 1H), 8.02 (d, 1H), 7.31-7.19 (m, 5H), 6.90-6.90 (m, 1H), 5.12-5.08 (m, 1H), 4.71 (dd, 1H), 4.01 (d, 1H), 3.57-3.50 (m, 4H), 3.30-3.25 (m, 4H), 3.09-3.05 (m, 1H), 2.95 (dd, 1H), 2.71 (dd, 1H), 2.35-2.30 (m, 1H), 1.11 (d, 3H), 0.82 (d, 3H), 0.73 (d, 3H).

MS (ESI+): m/z (%)=493 (M+H⁺) (100).

HPLC (method 4): R_f=2.02 min.

The following compounds are synthesized using general procedure C:

Example 9

N-((1s)-2-Methyl-1-{[(3R,4S)-4-methyl-2,5-dioxo-3-pyrrolidinyl]carbonyl}propyl)-3-{[(1-naphthylamino)carbonyl]amino}-3-phenylpropionamide

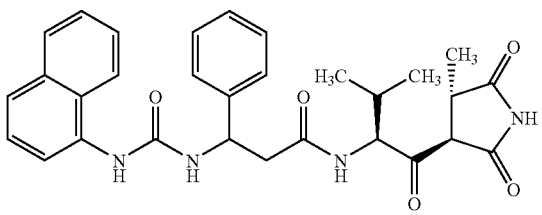

2 diastereomers $^1$H NMR (300 MHz, $d_6$-DMSO): δ=11.31 (s, 1H), 8.74+8.62 (2×s, 1H), 8.20-8.05 (m, 2H), 7.99-7.85 (m, 2H), 7.57-7.48 (m, 3H), 7.42-7.18 (m, 7H), 5.28-5.17 (m, 1H), 4.60 (dd, 1H), 3.98+3.95 (2×d, 1H), 2.96-2.86 (m, 2H), 2.78-2.68 (m, 1H), 2.32-2.20 (m, 1H), 1.11 (2×d, 3H), 0.78-0.65 (m, 6H).

MS (ESI+): m/z (%)=529 (M+H$^+$) (100).

HPLC (method 5): $R_t$=3.87 min.

Example 10

3-[({[4-Chloro-3-(trifluoromethyl)phenyl]amino}carbonyl)amino]-N-((1S)-2-methyl-1-{[(3R,4S-4-methyl-2,5-dioxo-3-pyrrolidinyl]carbonyl}propyl)-3-phenylpropion-amide

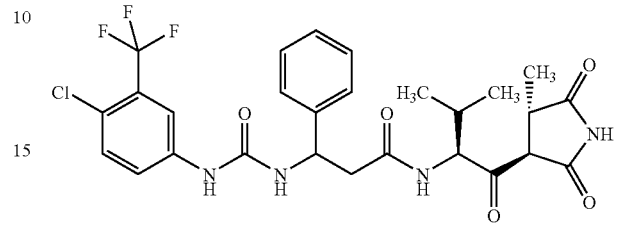

2 diastereomers $^1$H NMR (300 MHz, $d_6$-DMSO): δ=11.32 (s, 1H), 9.31+9.10 (2×s, 1H), 8.20-8.12 (m, 1H), 8.03 (s, 1H), 7.52-7.49 (m, 1H), 7.34-7.00 (m, 7H), 5.19-5.08 (m, 1H), 4.61-4.55 (m, 1H), 3.96+3.94 (2×d, 1H), 2.98-2.62 (m, 3H), 2.30-2.20 (m, 1H), 1.10 (2×d, 3H), 0.76-0.62 (m, 6H).

MS (ESI+): m/z (%)=581 (M+H$^+$) (100).

The compounds of Table 1 are synthesized using general procedure C:

| Example | Structure | Molecular weight | MS | HPLC |
|---|---|---|---|---|
| 11 | 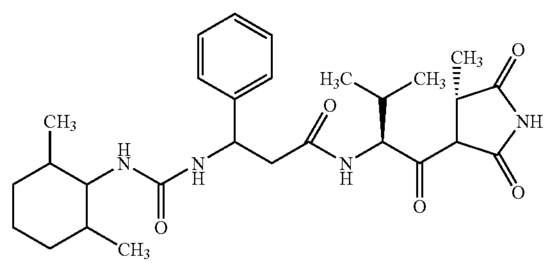 | 512.65 | MS (ES+), m/z (%): 513 (M + H)$^+$ (100) | HPLC (method 8): Rt = 2.60 min |
| 12 | 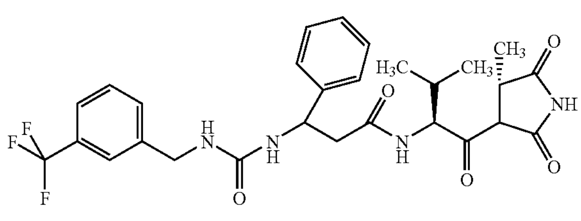 | 560.57 | MS (ES+), m/z (%): 583 (M + Na)$^+$ (100) | HPLC (method 5): Rt = 3.94 min |
| 13 | 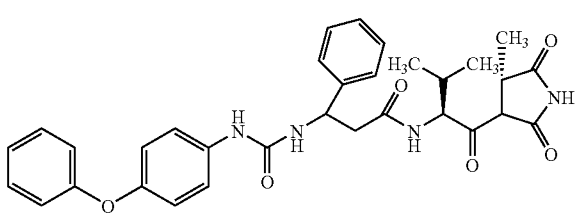 | 570.64 | MS (ES+), m/z (%): 593 (M + Na)$^+$ (100) | HPLC (method 5): Rt = 4.21 min |

-continued

| Example | Structure | Molecular weight | MS | HPLC |
|---|---|---|---|---|
| 14 | 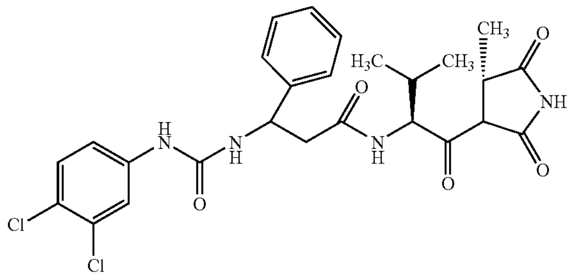 | 547.44 | MS (ES+), m/z (%): 547 (M + H)+ (100) | HPLC (method 8): Rt = 2.71 min |
| 15 | 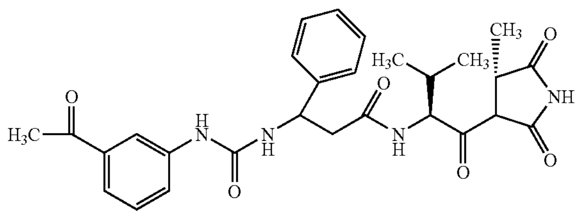 | 520.58 | MS (ES+), m/z (%): 521 (M + H)+ (100) | HPLC (method 8): Rt = 2.46 min |
| 16 | 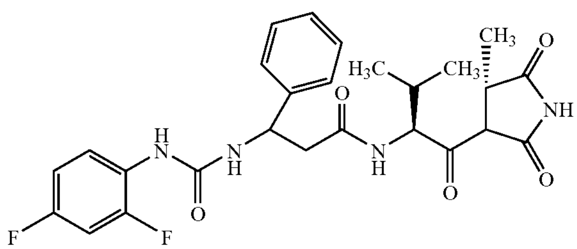 | 514.53 | MS (ES+), m/z (%): 515 (M + H)+ (100) | HPLC (method 8): Rt = 2.46 min |
| 17 | 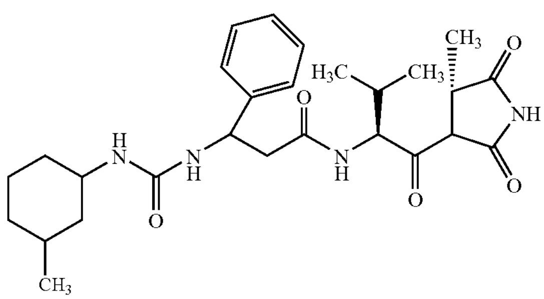 | 498.62 | MS (ES+), m/z (%): 499 (M + H)+ (100) | HPLC (method 5): Rt = 3.89 min |
| 18 | 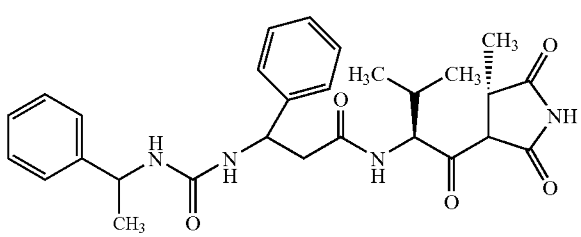 | 506.60 | MS (ES+), m/z (%): 507 (M + H)+ (100) | HPLC (method 5): Rt = 3.71 min |

The compounds of Table 2 are synthesized using general procedure D:
| Example | Structure | Molecular weight | MS | HPLC |
|---|---|---|---|---|
| 19 | 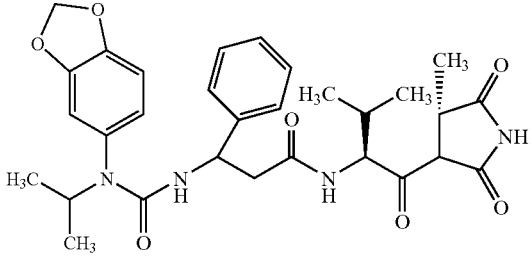 | 564.64 | MS (ES+), m/z (%): 565 (M + H)+ (100) | HPLC (method 5): Rt = 3.96 min |
| 20 | 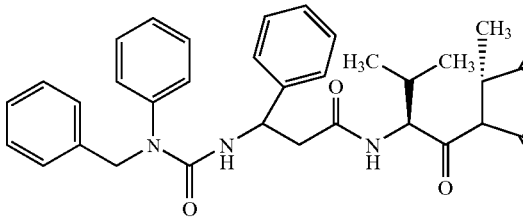 | 568.67 | MS (ES+), m/z (%): 569 (M + H)+ (50) | HPLC (method 5): Rt = 4.23 min |
| 21 | 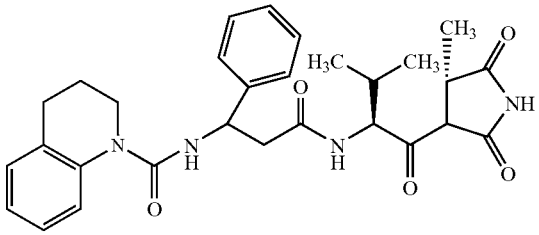 | 518.61 | MS (ES+), m/z (%): 519 (M + H)+ (100) | HPLC (method 5): Rt = 3.94 min |
| 22 | 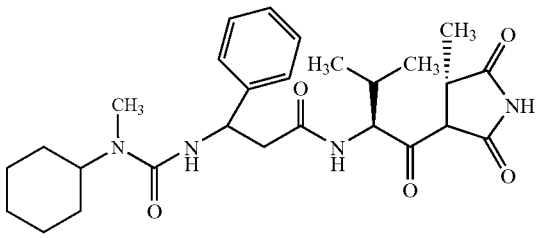 | 498.62 | MS (ES+), m/z (%): 499 (M + H)+ (100) | HPLC (method 5): Rt = 3.91 min |
| 23 | 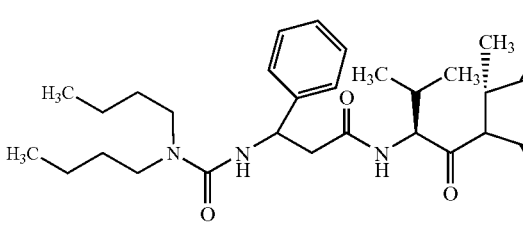 | 514.66 | MS (ES+), m/z (%): 515 (M + H)+ (100) | HPLC (method 5): Rt = 4.35 min |
| 24 | 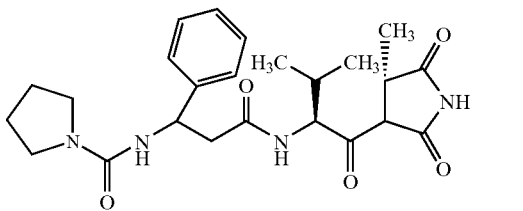 | 456.54 | MS (ES+), m/z (%): 457 (M + H)+ (100) | HPLC (method 5): Rt = 3.46 min |

-continued

| Example | Structure | Molecular weight | MS | HPLC |
|---|---|---|---|---|
| 25 | 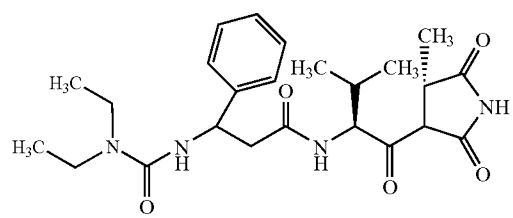 | 458.56 | MS (ES+), m/z (%): 459 (M + H)+ (100) | HPLC (method 5): Rt = 3.64 min |
| 26 | 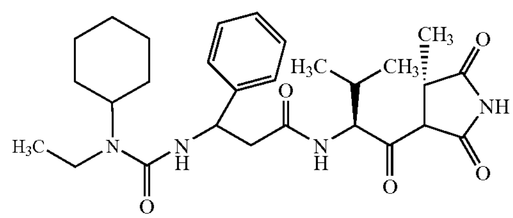 | 512.65 | MS (ES+), m/z (%): 513 (M + H)+ (100) | HPLC (method 5): Rt = 4.11 min +4.22 min |
| 27 | 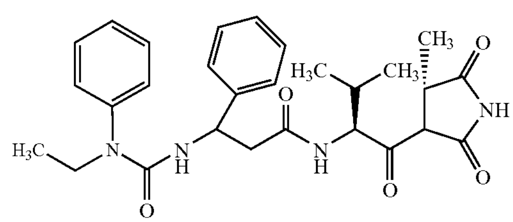 | 506.60 | MS (ES+), m/z (%): 507 (M + H)+ (100) | HPLC (method 5): Rt = 3.86 min |

General Procedure H

Acylation of 3-[2-aminoalkanoyl]-2,5-pyrrolidinedione hydrochloride derivatives with carboxylic acid derivatives

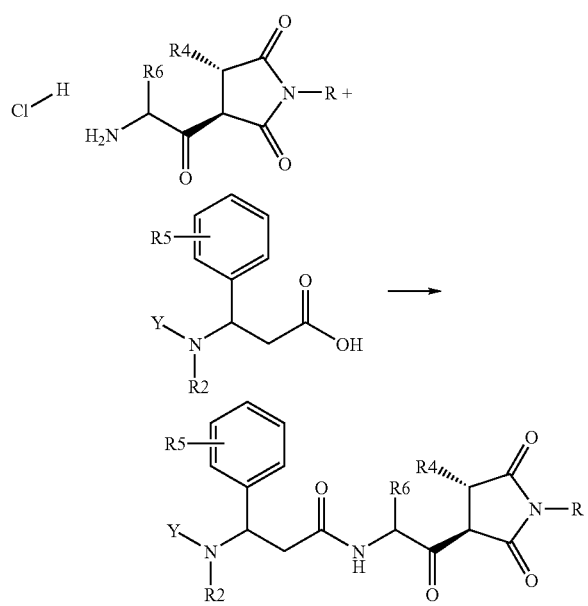

A solution of the carboxylic acid derivative (1.2-1.5 eq.) in absolute dichloromethane or a mixture (5:1 to 1:1) of absolute dichloromethane and N,N-dimethylformamide (about 0.1 to 0.3 mol/l) is admixed at 0° C. first with an equimolar amount of HATU and then with the 3-[2-aminoalkanoyl]-2,5-pyrrolidinedione hydrochloride derivative (1 eq., optionally as a solution in N,N-dimethylformamide or dichloromethane/N, N-dimethylformamide mixtures). Subsequently at 0° C. a solution of 2.5-3.5 eq. of diisopropylethylamine in a 1:1 mixture of absolute dichloromethane and N,N-dimethylformamide (0.2-1 mol/l) is added dropwise over a period of 1 h. When the addition has been made the reaction mixture is stirred at 0° C. for a further 30 minutes and then at room temperature overnight, before being concentrated in vacuo. The product can be obtained by chromatography on silica gel (mobile phases: mixtures of cyclohexane/ethyl acetate or mixtures of dichloromethane and ethanol) or by RP-HPLC (mobile phases: variable gradients of water and acetonitrile) or, alternatively, by a combination of both methods.

Alternatively the reaction may also take place according to the following method:

A solution of the 3-[2-aminoalkanoyl]-2,5-pyrrolidinedione hydrochloride derivative (1 eq.) in absolute dichloromethane or a mixture (5:1 to 1:1) of absolute dichloromethane and N,N-dimethylformamide (about 0.1 to 0.3 mol/l) is admixed with the carboxylic acid derivative (1.1-1.5 eq.), triethylamine (3 eq.), HOBt (3 eq.) and, finally, 1.2 eq. of EDC. The reaction mixture is stirred at room temperature (2 h to overnight), before being concentrated in vacuo. The residue is taken up in ethyl acetate or dichloromethane and the organic phase is washed with water, saturated sodium hydrogencarbonate solution and saturated sodium chloride solution, dried over sodium sulfate, filtered and concentrated. The product can be purified by chromatography on silica gel (mobile phases: mixtures of cyclohexane/ethyl acetate or mixtures of dichloromethane and ethanol) or by RP-HPLC (mobile phases: variable gradients of water and acetonitrile) or, alternatively, by a combination of both methods.

General procedure H can be used to give the following compounds:

| Example | Structure | MW | MS | HPLC |
|---|---|---|---|---|
| 28 | 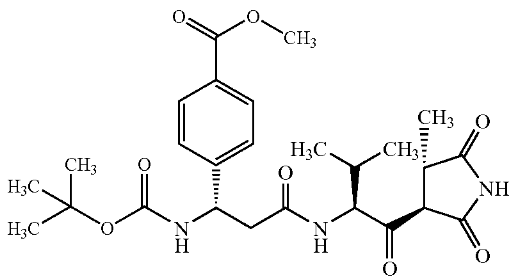 | 517.58 | MS (ES+), m/z (%): 518 (M + H)+ | HPLC (method 8): $R_t$ = 2.60 min |
| 29 | 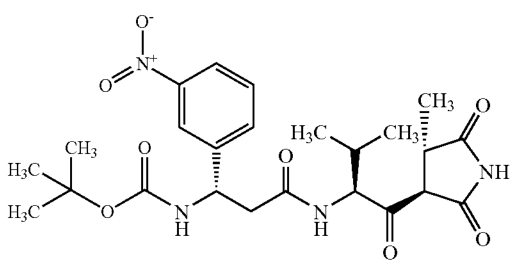 | 504.54 | MS (ES−), m/z (%): 503 (M − H)− | HPLC (method 6): $R_t$ = 3.99 min |
| 30 | 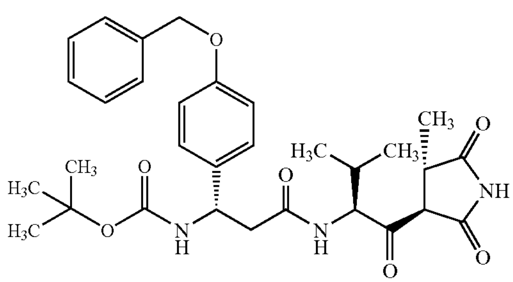 | 565.67 | MS (ES+), m/z (%): 566 (M + H)+ | HPLC (method 16): $R_t$ = 3.45 min |
| 31 | 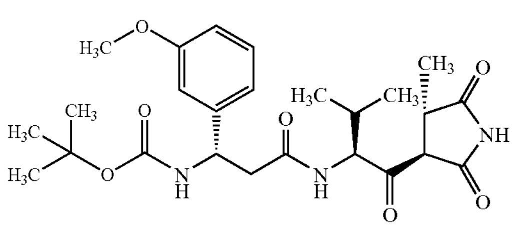 | 489.57 | MS (ES+), m/z (%): 490 (M + H)+ | HPLC (method 16): $R_t$ = 2.90 min |
| 32 | 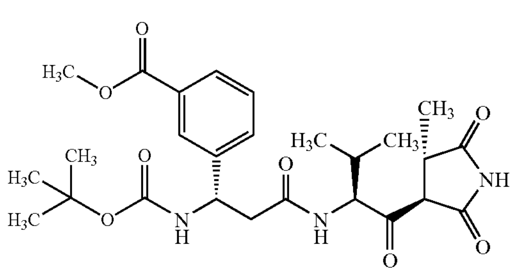 | 517.58 | MS (ES+), m/z (%): 518 (M + H)+ | HPLC (method 16): $R_t$ = 2.89 min |

-continued

| Example | Structure | MW | MS | HPLC |
|---|---|---|---|---|
| 33 | 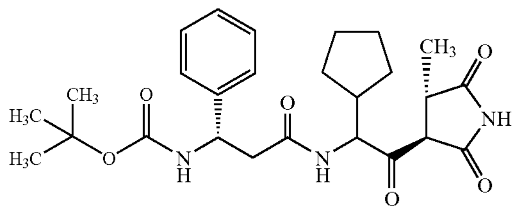 | 485.58 | MS (ES−), m/z (%): 484 (M − H)⁻ | HPLC (method 17): R_t = 3.63 min |
| 34 | 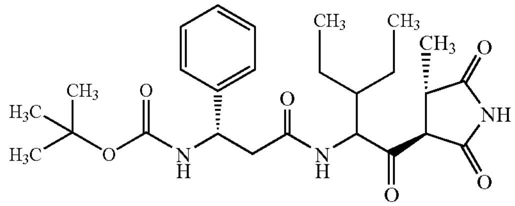 | 487.59 | MS (ES+), m/z (%): 488 (M + H)⁺ | HPLC (method 17): R_t = 3.73 min |

General Procedure J

Reaction of acylalkylamino-substituted 3-[2-aminoalkanoyl]-2,5-pyrrolidine-dione hydrochloride derivatives with chloroformic esters

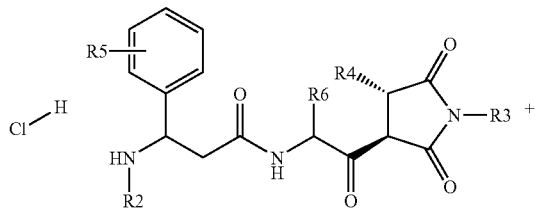

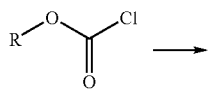

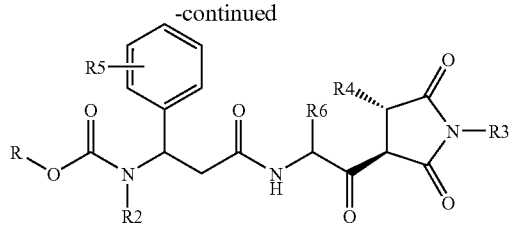

The amine hydrochloride is introduced in tetrahydrofuran (about 0.1 mol/l) and admixed with triethylamine (2 eq.) and the chloroformic ester (1.2 eq.). The reaction mixture is stirred at room temperature overnight. If complete reaction has not taken place by that time (TLC monitoring), stirring is carried out at 40° C. for a further night. Thereafter the reaction mixture is concentrated and the residue is taken up in dichloromethane and water and filtered through an Extrelut cartridge (Merck, Germany). The filtrate is concentrated and the residue is purified by RP-HPLC (mobile phases: variable gradients with acetonitrile and water+0.3 ml 37% hydrochloric acid/l).

General procedure J can be used to give the following compounds:

| Example | Structure | MW | MS | HPLC |
|---|---|---|---|---|
| 35 | 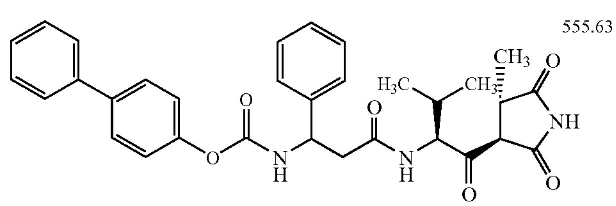 | 555.63 | MS (ES+), m/z (%): 556 (M + H)⁺ | HPLC (method 10): R_t = 3.63 min |

-continued

| Example | Structure | MW | MS | HPLC |
|---|---|---|---|---|
| 36 | 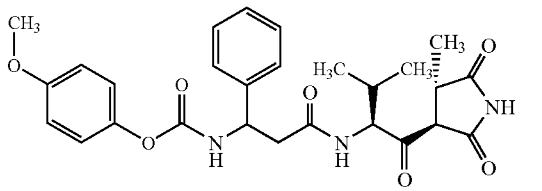 | 509.56 | MS (ES+), m/z (%): 510 (M + H)+ | HPLC (method 10): $R_t$ = 3.13 min |
| 37 | 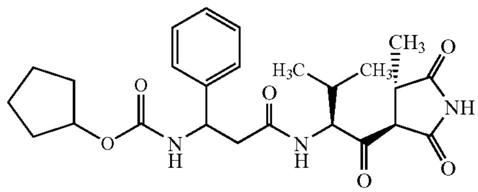 | 471.55 | MS (ES−), m/z (%): 470 (M − H)− | HPLC (method 10): $R_t$ = 3.20 min |
| 38 | 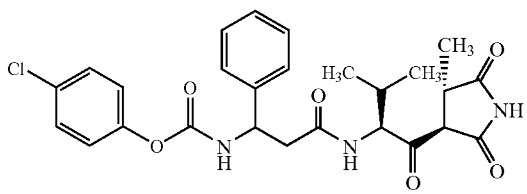 | 513.98 | MS (ES+), m/z (%): 536 (M + Na)+ | HPLC (method 5): $R_t$ = 4.28 min |
| 39 | 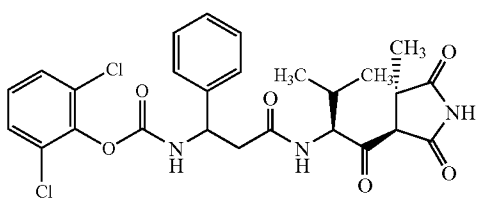 | 548.42 | MS (ES+), m/z (%): 548 (M + H)+ | HPLC (method 10): $R_t$ = 3.37 min |
| 40 | 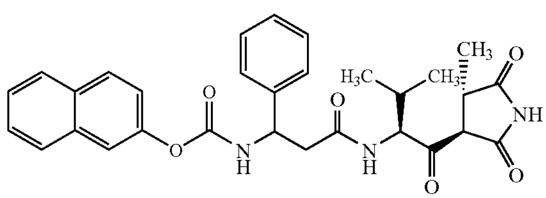 | 529.59 | MS (ES+), m/z (%): 530 (M + H)+ | HPLC (method 10): $R_t$ = 3.45 min |
| 41 | 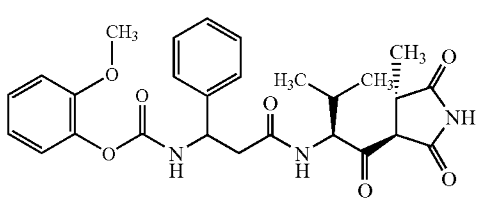 | 509.56 | MS (ES+), m/z (%): 532 (M + Na)+ | HPLC (method 5): $R_t$ = 3.97 min |
| 42 | 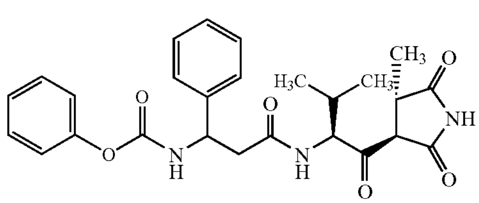 | 479.53 | MS (ES+), m/z (%): 480 (M + H)+ | HPLC (method 10): $R_t$ = 3.13 min |

-continued

| Example | Structure | MW | MS | HPLC |
|---|---|---|---|---|
| 43 | 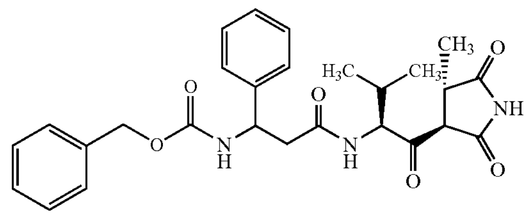 | 493.56 | MS (ES+), m/z (%): 516 (M + Na)+ | HPLC (method 5): $R_t$ = 4.11 min |
| 44 | 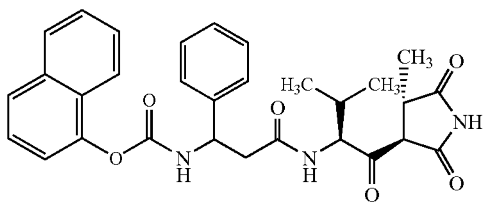 | 529.59 | MS (ES+), m/z (%): 530 (M + H)+ | HPLC (method 10): $R_t$ = 3.40 min |

General Procedure K

Preparation of sulfonamide derivatives starting from substituted (3R,4S)-3-[(2S)-2-amino-3-methylbutanoyl]4-methyl-2,5-pyrrolidinedione derivatives in the form of their hydrochlorides with sulfonyl chlorides

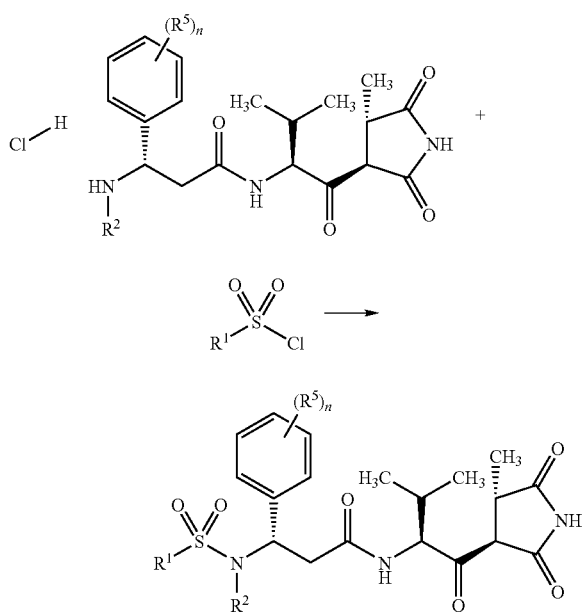

The hydrochloride (1.0 eq.) in absolute dichloroethane (about 0.1 mol/l) is admixed at room temperature with about 2.4 eq. of polymer-bound amine base (PS-DIEA from Argonaut Technologies, loading: about 3.8 mmol/g resin) and sulfonyl chloride (about 1.2 eq.). The mixture is shaken overnight at room temperature and then filtered. The filtrate is applied to a silica gel cartridge. The product can be eluted with mixtures of dichloromethane and methanol (typically 95:5). Further purification by RP-HPLC is possible where appropriate.

Alternatively the hydrochloride can be dissolved in N,N-dimethylformamide (about 0.1 mol/l) and the solution admixed with 2 eq. of triethylamine and 1 eq of the sulfonyl chloride. The reaction mixture is stirred at room temperature overnight, concentrated and then purified by RP-HPLC (mobile phase: water-acetonitrile, gradient).

Example 45

(3S)-N-((1S)-2-Methyl-1-{[(3R,4S)-4-methyl-2,5-dioxo-3-pyrrolidinyl]carbonyl}-propyl)-3-[(pentylsulfonyl)amino]-3-phenylpropionamide Synthesis is by general procedure K.

$^1$H NMR (400 MHz, $d_6$-DMSO): δ=11.31 (s, 1H), 8.18 (d, 1H), 7.74 (d, 1H), 7.40-7.21 (m, 5H), 4.78-4.69 (m, 1H), 4.53 (dd, 1H), 3.83 (d, 1H), 2.90-2.62 (m, about 5H), 2.32-2.26 (m, 1H), 1.45-1.05 (m, about 6H), 1.01 (d, 3H), 0.85 (d, 3H), 0.80-0.75 (m, 6H).

MS (ESI+): m/z (%)=494 (M+H+) (100).

HPLC (method 4): $R_t$=2.47 min.

Example 46

(3S)-N-((1S)-2-Methyl-1-{[(3R,4S)4-methyl-2,5-dioxo-3-pyrrolidinyl]carbonyl}-propyl)-3-[(octylsulfonyl)amino]-3-phenylpropionaminde

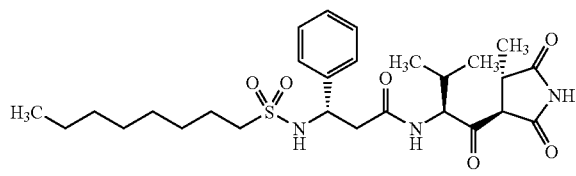

Synthesis is by general procedure K.
MS (ESI+): m/z (%)=536 (M+H$^+$) (100).
HPLC (method 4): R$_t$=2.80 min.

Example 47

(3S)-N-((1S)-2-Methyl-1-{[(3R,4S)-4-methyl-2,5-dioxo-3-pyrrolidinyl]carbonyl}-propyl)-3-phenyl-3-({[(E)-2-phenylethenyl]sulfonyl}amino)propionamide

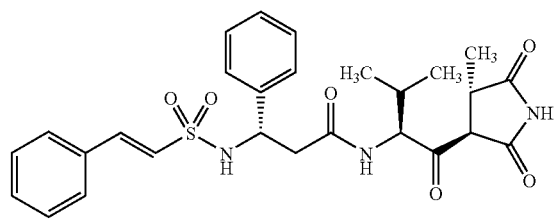

Synthesis is by general procedure K.
$^1$H NMR (300 MHz, d$_6$-DMSO): δ=11.30 (br. s, 1H), 8.14 (d, 1H), 7.97 (d, 1H), 7.46-7.10 (m, 11H), 6.70 (d, 1H), 4.81-4.68 (m, 1H), 4.51 (dd, 1H), 3.80 (d, 1H), 2.88-2.62 (m, 3H), 2.30-2.19 (m, 1H), 1.02 (d, 3H), 0.78 (d, 3H), 0.74 (d, 3H).
MS (ESI+): m/z (%)=526 (M+H$^+$) (100).
HPLC (method 5): R$_t$=3.91 min.

Example 48

(3S)-3-[(1,1'-Biphenyl-4-ylsulfonyl)amino]-N-((1S)-2-methyl-1-{[(3R,4S)-4-methyl-2,5-dioxo-3-pyrrolidinyl]carbonyl}propyl)-3-phenylpropionamide

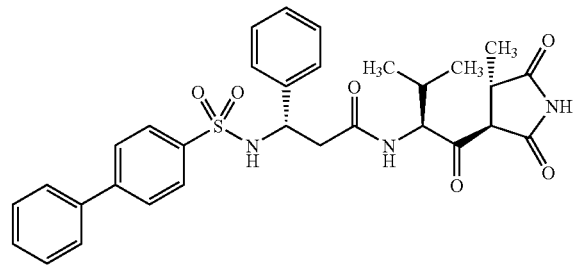

Synthesis is by general procedure K.
$^1$H NMR (300 MHz, d$_6$-DMSO): δ=11.30 (br. s, 1H), 8.27 (d, 1H), 8.11 (d, 1H), 7.68-7.60 (m, 6H), 7.52-7.39 (m, 3H), 7.13-7.01 (m, 5H), 4.80-4.68 (m, 1H), 4.48 (dd, 1H), 3.75 (d, 1H), 2.86-2.78 (m, 1H), 2.65 (d, 2H), 2.28-2.18 (m, 1H), 0.99 (d, 3H), 0.79 (d, 3H), 0.73 (d, 3H).
MS (ESI+): m/z (%)=576 (M+H$^+$) (100).
HPLC (method 5): R$_t$=4.23 min.

Example 49 tert-Butyl ((S)-2-{(S)-2-methyl-1-[1-((3R,4S)-4-methyl-2,5-dioxo-pyrrolidin-3-yl)-methanoyl]propylcarbamoyl}-1-phenylethyl)carbamate

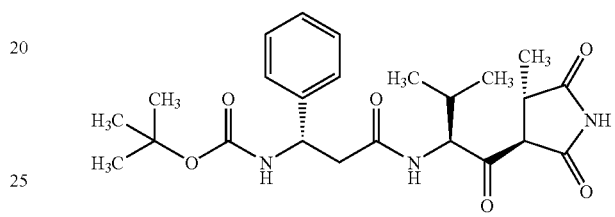

Synthesis is by general procedure A.
$^1$H-NMR (400 MHz, d$_6$-DMSO):δ=11.45 (s, 1H), 7.98 (d, 1H), 7.31-7.24 (m, 5H), 7.20 (br. s, 1H), 4.88-4.82 (br. s, 1H), 4.69 (br. s, 1H), 3.98 (d, 1H), 2.95-2.89 (m, 1H), 2.77-2.69 (m, 1H), 2.51-2.44 (m, 1H), 2.35-2.29 (m, 1H), 1.10 (d, 3H), 0.85 (d, 3H), 0.78 (d, 3H).
MS (ESI+): m/z (%)=460 (M+H$^+$) (100).
HPLC (method 6): R$_t$=3.90 min.

C. Examples of pharmaceutical compositions

The compounds of the invention can be converted into pharmaceutical preparations as follows:

Tablet:

Composition:

100 mg of the compound from Example 1, 50 mg of lactose (monohydrate), 50 mg of corn starch (native), 10 mg of polyvinylpyrrolidone (PVP 25) (from BASF, Ludwigshafen, Germany) und 2 mg of magnesium stearate.

Tablet weight 212 mg. Diameter 8 mm, radius of curvature 12 mm.

Production:

The mixture of active ingredient, lactone and starch is granulated with a 5% strength solution (m/m) of the PVP in water. The granules are dried and then mixed with the magnesium stearate for 5 minutes. This mixture is compressed using a conventional tablet press (see above for tablet format). As a guideline for compression a pressing force of 15 kN is used.

Suspension for oral administration:

Composition:

1000 mg of the compound from Example 1, 1000 mg of ethanol (96%), 400 mg of Rhodigel (xanthan gum from FMC, Pa., USA) and 99 g of water. 10 ml of oral suspension correspond to a single dose of 100 mg of the compound of the invention.

Production:

The Rhodigel is suspended in ethanol, and the active ingredient is added to the suspension. The water is added with stirring. The mixture is stirred for about 6 h until the Rhodigel has finished swelling.

The invention claimed is:
1. A compound of formula (I)

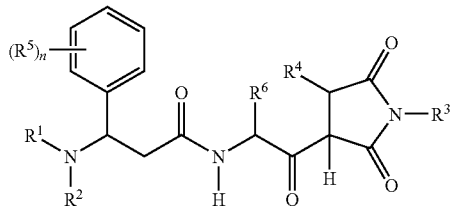

in which
$R^1$ is a group

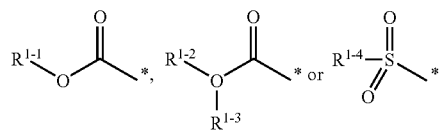

where
$R^{1-1}$ is alkyl, cycloalkyl or aryl,
where
$R^{1-1}$ can optionally be substituted by from 1 to 3 substituents $R^{1-1-1}$, $R^{1-1-1}$ being selected independently at each occurrence from the group consisting of halogen, alkyl, aryl, alkoxy, phenoxy, amino, monoalkylamino, dialkylamino, aminocarbonyl, monoalkylaminocarbonyl, dialkylaminocarbonyl, carboxyl, alkoxycarbonyl, alkylcarbonyl, heteroaryl and heterocyclyl,
$R^{1-2}$ and $R^{1-3}$ are identical or different and are hydrogen, alkyl, alkenyl, alkynyl, cycloalkyl, aryl, heteroaryl or heterocyclyl,
where
$R^{1-2}$ can optionally be substituted by from 1 to 3 substituents $R^{1-2-1}$, $R^{1-2-1}$ being selected independently at each occurrence from the group consisting of halogen, trifluoromethyl, trifluoromethoxy, nitro, amino, alkyl, monoalkylamino, dialkylamino, cycloalkyl, aryl, heteroaryl, heterocyclyl, hydroxyl, alkoxy, phenoxy, carboxyl, alkoxycarbonyl, ailkylcarbonyl, aminocarbonyl, monoalkylaminocarbonyl, dialkylaminocarbonyl, aminosulfonyl, alkylamino-sulfonyl, dialkylaminosulfonyl, arylaminosulfonyl, heterocyclylaminosulfonyl, heteroarylaminosulfonyl, aminocarbonylamino, hydroxycarbonylamino and alkoxycarbonylamino, it being possible for aryl and heteroaryl to be substituted by from 1 to 2 substituents selected independently of one another from the group consisting of halogen, hydroxyl, alkyl, alkoxy, trifluoromethyl, trifluoromethoxy, nitro, amino, cyano, monoalkylamino and dialkylamino,
or
$R^{1-2}$ and $R^{1-3}$ together with the nitrogen atom to which they are attached form a heterocycle which can optionally be benzo-fused,
$R^{1-4}$ is alkyl, alkenyl, alkynyl, cycloalkyl or aryl, where
$R^{1-4}$ can optionally be substituted by from 1 to 3 substituents $R^{1-4-1}$, $R^{1-4-1}$ being selected independently at each occurrence from the group consisting of halogen, alkyl, aryl, amino, monoalkylamino, dialkylamino, aminocarbonyl, monoalkylaminocarbonyl, dialkylaminocarbonyl, carboxyl, alkoxycarbonyl, alkylcarbonyl, heteroaryl and heterocyclyl,
$R^2$ is hydrogen or methyl,
$R^3$ is hydrogen or $C_1$-$C_3$-alkyl,
$R^4$ is hydrogen or $C_1$-$C_3$-alkyl,
$R^5$ is selected from the group consisting of halogen, trifluoromethyl, trifluoromethoxy, nitro, amino, monoalkylamino, dialkylamino, hydroxyl, alkyl, alkoxy, carboxyl, alkoxycarbonyl, aminocarbonyl, monoalkylaminocarbonyl, dialkylaminocarbonyl, aryl and heteroaryl,
or
two substituents $R^5$ together with the carbon atoms to which they are attached form a cycloalkyl or heterocyclyl,
it being possible for this cycloalkyl or heterocyclyl to be substituted by 0, 1 or 2 substituents $R^{5-1}$, the substituents $R^{5-1}$ being selected independently of one another from the group consisting of halogen, alkyl, nitro, amino, trifluoromethyl, hydroxyl and alkoxy,
n is 0, 1, 2 or 3,
where if n is 2 or 3 the radicals $R^5$ can be identical or different,
$R^6$ is alkyl, cycloalkyl or heterocyclyl,
it being possible for $R^6$ to be substituted by 0, 1 or 2 substituents $R^{6-1}$, the substituents $R^{6-1}$ being selected independently of one another from the group consisting of halogen, nitro, amino, trifluoromethyl, hydroxyl, alkyl and alkoxy,
or a pharmaceutically acceptable salt thereof.
2. The compound of formula (I) of claim 1, in which
$R^{1-1}$ is alkyl, cycloalkyl or aryl,
where
$R^{1-1}$ can be optionally substituted by from 1 to 3 substituents $R^{1-1-1}$, $R^{1-1-1}$ being selected independently at each occurrence from the group consisting of halogen, alkyl, aryl and alkoxy,
$R^{1-2}$ and $R^{1-3}$ are identical or different and are hydrogen, alkyl, alkenyl, cycloalkyl, aryl or heteroaryl,
where
$R^{1-2}$ can be substituted by from 1 to 2 substituents $R^{1-2-1}$, $R^{1-2-1}$ being selected independently at each occurrence from the group consisting of halogen, trifluoromethyl, trifluoromethoxy, nitro, amino, alkyl, monoalkylamino, dialkylamino, cycloalkyl, aryl, heteroaryl, heterocyclyl, hydroxyl, alkoxy, phenoxy, alkylcarbonyl, aminocarbonyl, monoalkylaminocarbonyl, dialkylaminocarbonyl and aminosulfonyl, it being possible for aryl and heteroaryl to be substituted by from 1 to 2 substituents selected independently of one another from the group consisting of halogen, hydroxyl, alkoxy, trifluoromethyl, trifluoromethoxy, nitro and amino,
or $R^{1-2}$ and $R^{1-3}$ together with the nitrogen atom to which they are attached form a heterocycle which can optionally be benzo-fused,
$R^{1-4}$ is alkyl, alkenyl or aryl,
where
$R^{1-4}$ can optionally be substituted by from 1 to 3 substituents $R^{1-4-1}$, $R^{1-4-1}$ being selected independently at each occurrence from the group consisting of halogen, alkyl and aryl, $R^2$ is hydrogen,
$R^3$ is hydrogen or methyl,
$R^4$ is methyl,
$R^5$ is selected from the group consisting of fluorine, chlorine, trifluoromethyl, trifluoromethoxy, nitro, amino, monoalkylamino, dialkylamino, hydroxyl, alkyl, alkoxy, alkoxycarbonyl, aminocarbonyl, phenyl, and 5- to 6-membered heteroaryl,
or
two substituents $R^5$ together with the carbon atoms to which they are attached form a cycloalkyl or heterocyclyl,
n is 0, 1 or 2,
where if n is 2 the radicals $R^5$ can be identical or different,
$R^6$ is alkyl or cycloalkyl,
where $R^6$ can be substituted by 0, 1 or 2 substituents $R^{6-1}$, the substituents $R^{6-1}$ being selected independently of one another from the group consisting of halogen, trifluoromethyl and alkoxy,
or a pharmaceutically acceptable salt, solvate or hydrate thereof.

3. The compound of formula (I) of claim 1, in which
$R^{1-1}$ is $C_1$-$C_4$-alkyl, cyclopentyl, cyclohexyl, phenyl or naphthyl,
where
$R^{1-1}$ can optionally be substituted by from 1 to 2 substituents $R^{1-2-1}$, $R^{1-1-1}$ being selected independently at each occurrence from the group consisting of fluorine, chlorine, methyl, ethyl, phenyl, methoxy and ethoxy,
$R^{1-2}$ alkyl, cycloalkyl, aryl or heteroaryl, it being possible for $R^{1-2}$ to be optionally substituted by 1 substituent $R^{1-2-1}$, $R^{1-2-1}$ being selected from the group consisting of fluorine, chlorine, trifluoromethyl, amino, alkyl, monoalkylamino, dialkylamino, alkylcarbonyl. aryl, heteroaryl, hydroxyl, methoxy and phenoxy, it being possible for aryl and heteroaryl to be substituted by 1 substituent selected from the group consisting of halogen, methoxy, trifluoromethyl and amino,
$R^{1-3}$ is hydrogen or methyl,
or $R^{1-2}$ and $R^{1-3}$ together with the nitrogen atom to which they are attached form a heterocycle which can optionally be benzo-fused,
$R^{1-4}$ is alkyl, alkenyl or phenyl,
where
$R^{1-4}$ can optionally be substituted by 1 substituent $R^{1-4-1}$, $R^{1-4-1}$ being selected from the group consisting of fluorine, chlorine and phenyl,
$R^2$ is hydrogen,
$R^3$ is hydrogen,
$R^4$ is methyl,
$R^5$ is selected from the group consisting of fluorine, chlorine, trifluoromethyl, alkoxy, methoxycarbonyl, $C_1$-$C_4$-alkyl, phenyl and pyridyl,
n is 0, 1 or 2,
where if n is 2 the radicals $R^5$ can be identical or different,
$R^6$ is isopropyl, isobutyl, isopentyl or cyclopentyl,
or a pharmaceutically acceptable salt, thereof.

4. The compound of formula (I) of any one of claims 1, 2 or 3 which has the general formula (Ic):

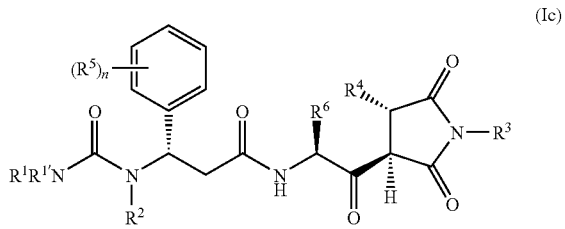

in which
$R^1$ to $R^6$ and n are as defined in claim 1.

5. The compound of formula (I) of any one of claim 1, 2 or 3, in which
$R^1$ is a group

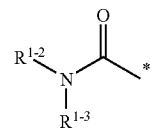

where
$R^{1-2}$ is alkyl, alkenyl, cycloalkyl or aryl,
it being possible for $R^{1-2}$ to be optionally substituted by from 1 to 2, in particular one, substituent(s) $R^{1-2-1}$, $R^{1-2-1}$ being selected from the group consisting of halogen, nitro, amino, alkyl, aryl, heteroaryl, hydroxyl, alkoxy, carboxyl, alkylcarbonyl, alkoxycarbonyl and aminocarbonyl, in particular selected from the group consisting of alkyl, aryl, heteroaryl and alkoxy.

6. The compound of formula (I) of claim 1, in which
$R^1$ is a group

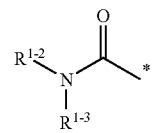

in which $R^{1-3}$ is hydrogen or methyl.

7. The compound of formula (I) of any one of claims 1, 2 or 3, in which $R^2$ is hydrogen.

8. The compound of formula (I) of any one of claims 1, 2 or 3, in which $R^3$ is hydrogen.

9. The compound of formula (I) of any one of claims 1, 2 or 3, in which $R^4$ is methyl.

10. The compound of formula (I) of any one of claims 1, 2 or 3, in which $R^5$ is hydrogen.

11. The compound of formula (I) of any one of claims 1, 2 or 3, in which $R^6$ is isopropyl.

12. A process for preparing a compound of formula (I), of claim 1, in which a compound of formula (II)

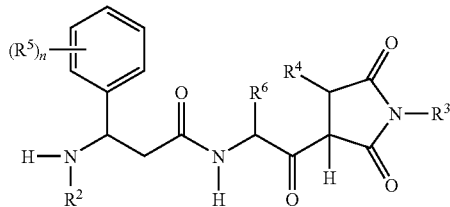

in which
R² to R⁶ and n are as defined in claim 1,
which may optionally be present in the form of a salt, or
for the case where
R¹ is a group

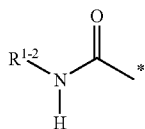

in which $R^{1-2}$ is as defined in claim 1,
[A] is reacted with a compound of formula (IIIa)

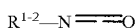 (IIIa)

in which
$R^{1-2}$ is as defined in claim 1,
or,
for the case where
R¹ is a group

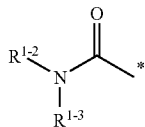

where
$R^{1-2}$ is as defined in claim 1,
$R^{1-3}$ is not hydrogen, or $R^{1-2}$ and $R^{1-3}$ form a heterocycle,
[B] is reacted with a compound of formula (IIIb)

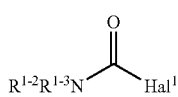 (IIIb)

in which
$R^{1-2}$ and $R^{1-3}$ are as defined in claim 1 and Hal¹ stands for a halide or another leaving group,
or,
for the case where
R¹ is a group

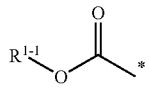

in which
$R^{1-1}$ is as defined in claim 1,
[C] is reacted with a compound of formula (IIIc)

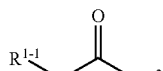 (IIIc)

in which
$R^{1-1}$ is as defined in claim 1 and Hal² stands for a halide or another leaving group,
or,
for the case where
R¹ is a group

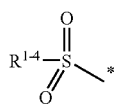

in which
$R^{1-4}$ is as defined in claim 1, or
[D] is reacted with a compound of formula (IIId)

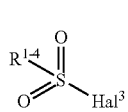 (IIId)

in which
$R^{1-4}$ is as defined above and Hal³ stands for a halide or another leaving group.

13. A pharmaceutical composition comprising a compound of formula (I) of any one of claims 1, 2 or 3 and a pharmaceutically acceptable excipient.

14. A method of treating a bacterial disease in a person or an animal comprising administering an antibacterially effective amount of at least one compound of any one of claims 1 to 3.

* * * * *